United States Patent [19]

Bromley et al.

[11] Patent Number: 5,646,010

[45] Date of Patent: *Jul. 8, 1997

[54] METHODS AND COMPOSITIONS FOR EXPRESSION OF COMPETENT EUKARYOTIC GENE PRODUCTS

[75] Inventors: Peter Bromley, Chene-Bougeries, Switzerland; Richard Voellmy, Miami, Fla.

[73] Assignee: Rockwell Property Limited, Isle of Man, United Kingdom

[*] Notice: The term of this patent shall not extend beyond the expiration date of Pat. No. 5,614,381.

[21] Appl. No.: 197,565

[22] Filed: Feb. 17, 1994

Related U.S. Application Data

[63] Continuation of Ser. No. 8,090, Jan. 22, 1993, abandoned, which is a continuation of Ser. No. 794,641, Nov. 18, 1991, abandoned, which is a continuation of Ser. No. 423,564, Oct. 16, 1989, abandoned, which is a continuation of Ser. No. 848,657, Apr. 4, 1986, abandoned, which is a continuation-in-part of Ser. No. 626,588, Jul. 3, 1984, abandoned, which is a continuation of Ser. No. 568,176, Jan. 5, 1984, abandoned, which is a continuation-in-part of Ser. No. 504,593, Jun. 17, 1983, abandoned, which is a continuation-in-part of Ser. No. 464,232, Feb. 7, 1983, abandoned.

[51] Int. Cl.$^6$ ............ C12P 21/02; C12N 15/85; C12N 5/16

[52] U.S. Cl. ............ 435/69.1; 435/172.3; 435/320.1; 435/69.2; 435/69.51; 435/69.52; 435/69.6; 435/252.3; 435/252.33; 435/325; 536/23.1; 536/24.1; 536/23.5; 935/6; 935/9; 935/10; 935/33

[58] Field of Search ............ 435/172.3, 320.1, 435/69.1, 69.2, 69.3, 69.4, 69.5, 69.51, 69.52, 69.6, 240.2, 252.3, 252.33, 91.1; 935/6, 9, 10, 33, 34, 41, 43; 536/23.1, 24.1, 24.2, 23.5, 23.51, 23.52, 23.53

[56] References Cited

U.S. PATENT DOCUMENTS

| | | | |
|---|---|---|---|
| 4,374,927 | 2/1983 | Sninsky et al. | 435/69.1 |
| 4,399,216 | 8/1983 | Axel et al. | 435/6 |
| 4,741,901 | 5/1988 | Levinson et al. | 424/227.1 |

OTHER PUBLICATIONS

Torok et al. 1982 in: Schlesinger et al. (eds.) "Heat Shock from Bacteria to Man", Cold Spring Harbor Laboratory, Cold Spring Harbor, NY, pp. 19–24.

Ernst et al. 1982 in: Schlesinger et al. (eds.) "Heat Shock from Bacteria to Man", Cold Spring Harbor Laboratory, Cold Spring Harbor, NY, pp. 215–225.

Ashburner, M. 1982 in: Schlesinger et al. (eds.) "Heat Shock from Bacteria to Man", Cold Spring Harbor Laboratory, Cold Spring Harbor, NY, pp. 1–9.

Old et al. 1985 in: "Principles of Gene Manipulation. An Introduction to Genetic Engineering", Blackwell Sci. Publ., Oxford, England, pp. 234–235.

Pelham et al, Cell vol. 30 pp. 517–528 (1982).

Torok et al, Nucleic Acids Res. vol. 8 pp. 3105–3123 (1980).

Voellmy et al, PNAS USA vol. 79 pp. 1776–1780 (1982).

Voellmy et al, Cell vol. 23 pp. 261–270 (1981).

Kaufman et al, Molecular and Cellular Biology vol. 2 pp. 1304–1319 Nov. 1982.

Voellmy et al, PNAS USA vol. 82 pp. 4949–4953 Aug. 1985.

Ellwood et al, Molecular and Cellular Biology vol. 4 pp. 1454–1459.

Corces et al, Heat Shock From Bacteria to Man, ed by Schlesinger et al, Cold Spring Har. Lab. pp. 27–34 (1982).

Pelman et al, Heat Shock From Bacteria to Man, ed by Schlesinger et al, Cold Spring Har. Lab. pp. 43–48 (1982).

Pelham et al, The EMBO Journal vol. 1 pp. 1473–1477 (1982).

Karch et al, J. Mol. Biol. vol. 148 pp. 219–230 (1981).

Corces et al, PNAS USA vol. 77 pp. 5390–5393 (1980).

Corces et al, PNAS USA vol. 78 pp. 7038–7042 (1981).

Ingalia et al, Cell vol. 21 pp. 669–679 Oct. 1980.

Hartman et al, Eukaryotic Viral Vectors ed, by Gluzman, Cold Spring Har. Lab. pp. 19–27 (1982).

Gething et al, Eukaryotic Viral Vectors ed by Gluzman, Cold Spring Har. Lab pp. 29–33 (1982).

Gheysen et al, Eukaryotic Viral Vectors ed. by Gluzman, Cold Spring Har. Lab pp. 35–39 (1982).

Nover, [review] "Expression of heat shock genes in homologous and heterologous systems," Enzyme Microb. Technol. 1987, vol. 9, Mar. pp. 130–144.

Amin et al, "The Heat Shock Consensus Sequence Is Not Sufficient for hsp70 Gene Expression in *Drosophila melanogaster*", Molecular and Cellular Biology, Jan. 1985, pp. 197–203.

McKenzie et al, "Localization of RNA from Heat-Induced Polysomes at Puff Sites in *Drosophila melanogaster*," Proc. Nat. Acad. Sci. USA, vol. 72, Mar. 1975, pp. 1117–1121.

Findly et al, "Regulated Transcription of the Genes for Actin and Heat-shock Proteins in Cultured Drosophila Cells," The Journal of Cell Biology, vol. 88, Feb. 1981, pp. 323–328.

Spradling et al, "Analysis of Drosophila mRNA by In Situ Hybridization: Sequences Transcribed in Normal and Heat Shocked Cultured Cells," Cell, vol. 4, pp. 395–404.

Spradling et al, "Messenger RNA in Heat-shocked Drosophila Cells," J. Mol. Biol. vol. 109, (1977), pp. 559–587.

Casadaban et al., 1980, J. Bacteriol., 143(2):971–980.

Lewin, R. 1987, Science 237, 1570.

(List continued on next page.)

*Primary Examiner*—Christopher S. F. Low
*Attorney, Agent, or Firm*—Cushman Darby & Cushman Intellectual Property Group of Pillsbury Madison & Sutro LLP

[57] ABSTRACT

Heat-shock gene control elements from different eukaryotic cells are utilized to provide expression of competent gene products in the same or similar eukaryotic as well as in procaryotic host cells. The control elements can be joined to a suitable eukaryotic replication system to form an expression vector, or may be joined to the gene of interest and introduced directly into the host genome.

14 Claims, 25 Drawing Sheets

OTHER PUBLICATIONS

Reeck et al. 1987 Cell. 50, 667.

Enzyme Microb. Technol., 1987, vol. 9, pp. 130–144.

Molecular and Cellular Biology, Jan. 1985, vol. 5, pp. 197–203.

Nature, Feb. 1986, vol. 319, pp. 555–559.

Cell, Sep. 12, 1986, vol. 46, pp. 807–817.

Science, Apr. 25, 1986, vol. 232, pp. 522–524.

Molecular and Cellular Biology, Jun. 1987, vol. 7, pp. 2188–2195.

Cell, Dec. 1982 (Part 2), vol. 31, pp. 593–603.

C. Kruger and B-J. Benecke, "Translation and Turnover of Drosophila Heat-shock and Nonheat-shock mRNAs", pp. 191–197.

Cell, Sep. 1985, vol. 42, pp. 527–537.

Nature, Oct. 1986, vol. 323, pp. 459–461.

Lutz Nover Ed. (1984) "Heat Shock Response of Eukaryotic Cells" pp. 28–34.

```
      -570      -560      -550      -540      -530      -520      -510
     GCTTTCCTCATATGTACATATGTATGTAAATATGTAAAATAAGTCGCAACTAAATTCTAATACATTTTTCAGAA

-500      -490      -480      -470      -460      -450      -440      -430
  TCTTAAATTAATTTTATCGTATATTAAAACAGAAGAAAGTCCGTTAATAGTTGATTTCATTAACTAAAAGTAC

-420      -410      -400      -390      -380      -370      -360
     AAAATAATCTTTAATACATATGCCGATCAGACATTTATTGGTTTAGAAGCGCAGTATTTTTTTGGCGGAAATAC
                          Sau3A
      -350      -340      -330      -320      -310      -300      -290
     GCATAACAAAGCGCTTCGATTATCTTTAACATAAGTTATTTAAGCAGCCGTATTTATAAAGAAATTTCCAAA

-280      -270      -260      -250      -240      -230      -220
     ATAAAGCATATATATAAATAAAGAATATTCTAGAATCCCAAAACAAAGCTGGTTATTGTGGTAGGTCAT
                                              XbaI
      -210      -200      -190      -180      -170      -160      -150
     TTGTTTGGCAGAAAGAAAACTCGAGAAATTTCTCTGGCCGTTATTCGTTATTCTCTCTTTTCTTTTTGGGT
                          XhoI
      -140      -130      -120      -110      -100       -90       -80
     CTCTCCCTCTCTGCACTAATGCTCTCTCACTCTGTCACACAGTAAACGGCATACTGCTCTCGTTGGTTC

-70       -60       -50       -40       -30       -20       -10
     CAGAGAGCGCGCCTCGAATGTTCGCGAAAAGAGCGCCGGAGTATAAATAGAGGCGCTTCGTCTACGG 1        10        20        30        40        50        60
     AGCGACAATTCAATTCAAACAAGCAAAGTGAACACGTCGCTAAGCGAAAGCTAAGCAAATAAACAAG
             ─────────────►
              1a
        70        80        90       100       110       120
     CGCAGCTGAACAAGCTAAACAATCTGCAGTAAAGTGCAAGTTAAAGTGAATCAATTAAAAGTAACCAG
                           PstI
      130       140       150       160       170       180       190
     CAACCAAGTAAATAAACTAACAACTGCAACTACTGAAATCTGCCAAGAAGTAATTATTGAATACAAGA 200       210       220       230       240       250       260
     AGAGAACTCTGAATACTTTCAACAAGTTACCGAGAAAGAAGAACTCACACACAATGCCTGCTATTGGA
                                                                ─────────►
                                                                       1b
      270       280
     ATCGATCTGGGCACCACC
     Sau3A
```

FIG. 2

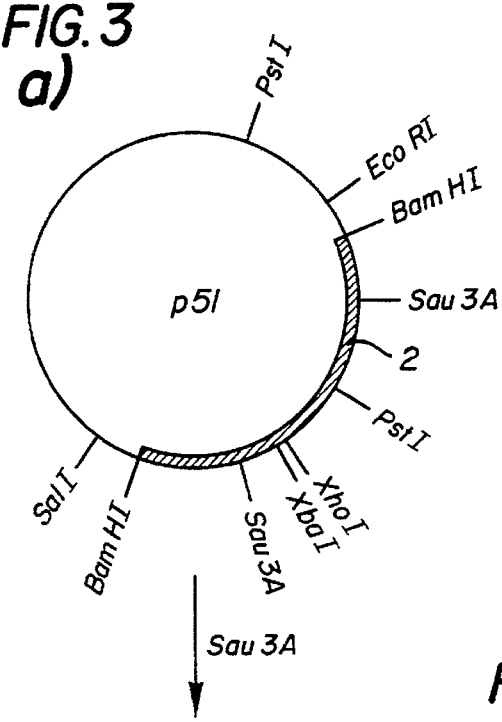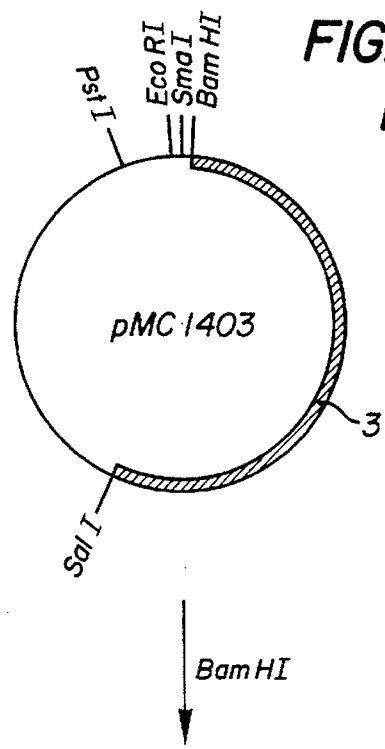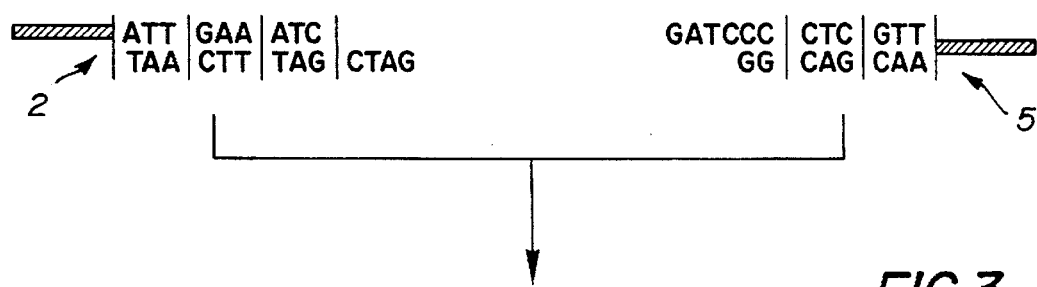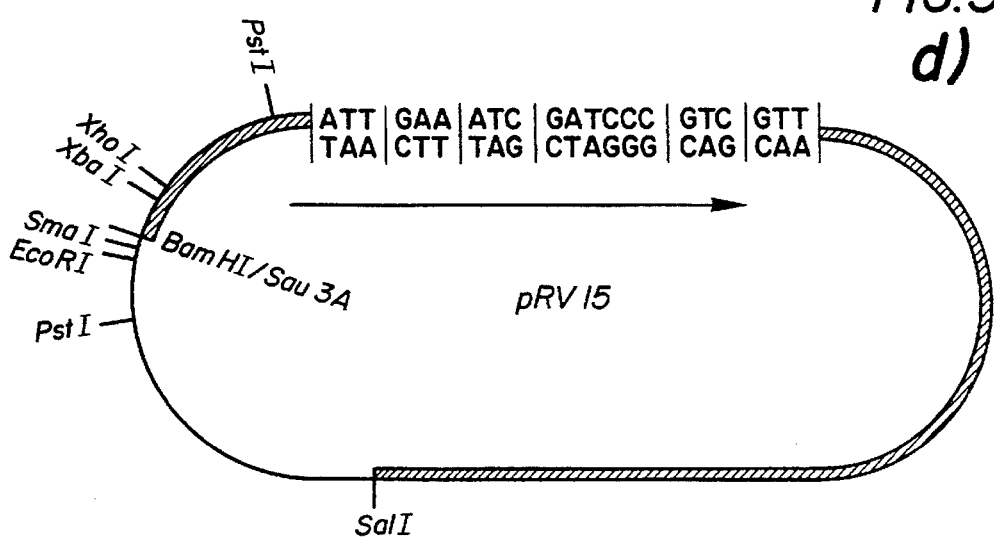

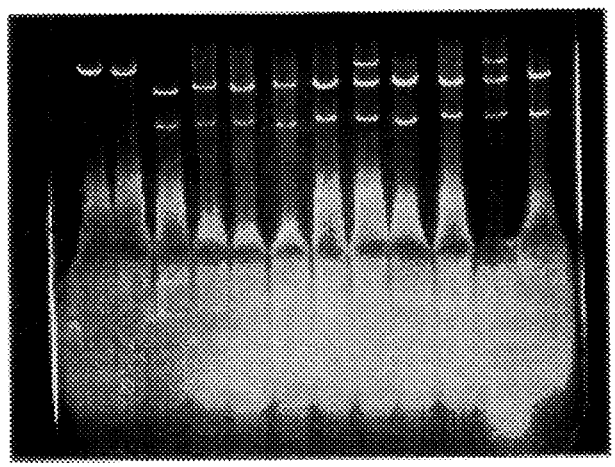
FIG. 5a
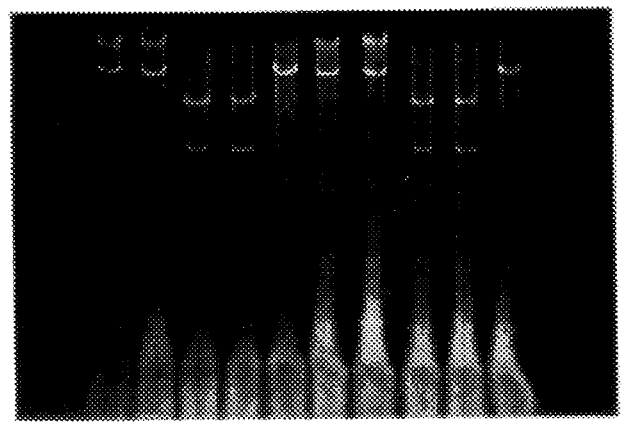
FIG. 5b
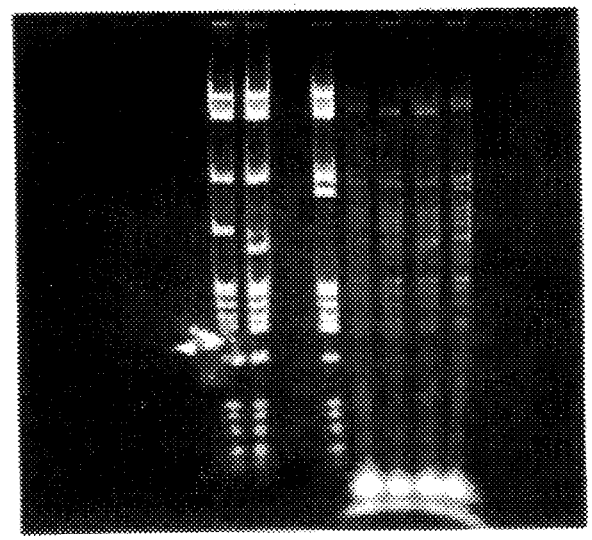
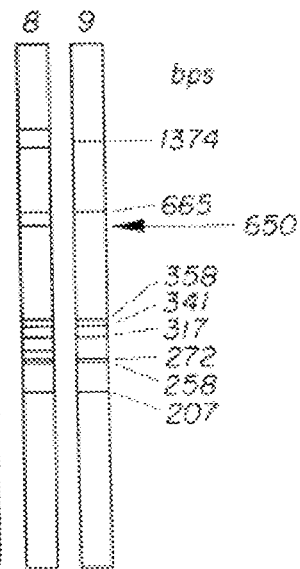
FIG. 5c

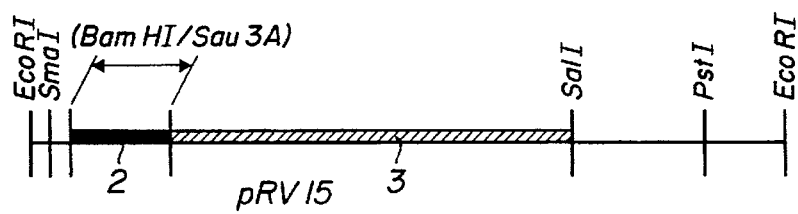
FIG. 7a
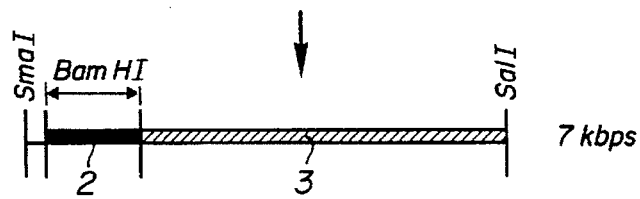
FIG. 7b
FIG. 7c
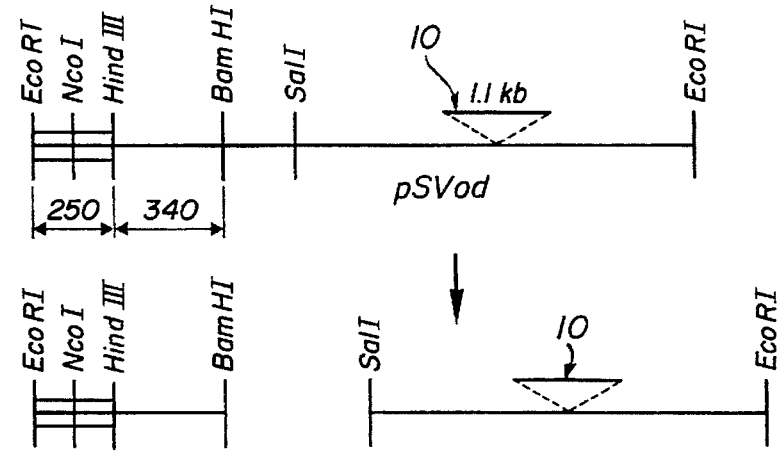
FIG. 7d
FIG. 7e
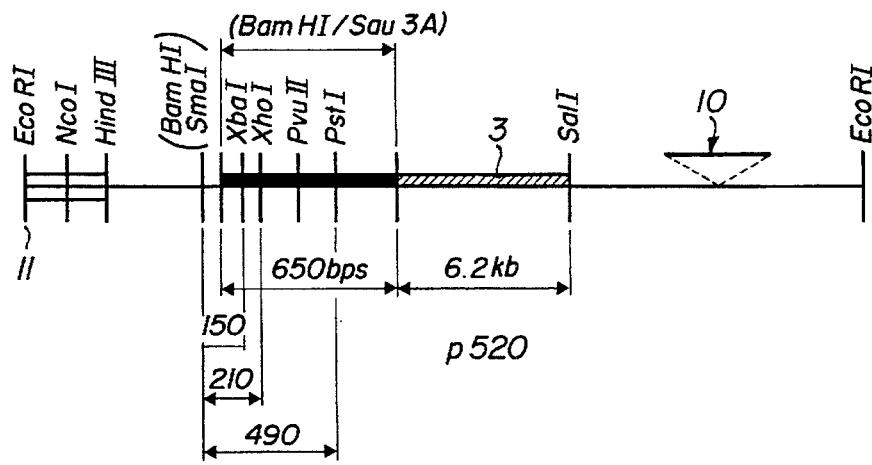

pA/PR8/34/ms/4.76 pR8l

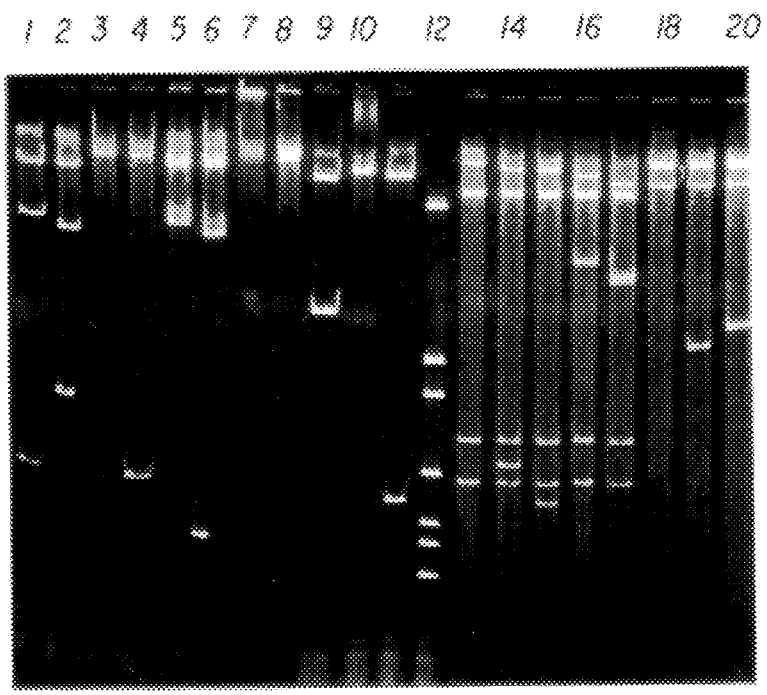
FIG. IIa

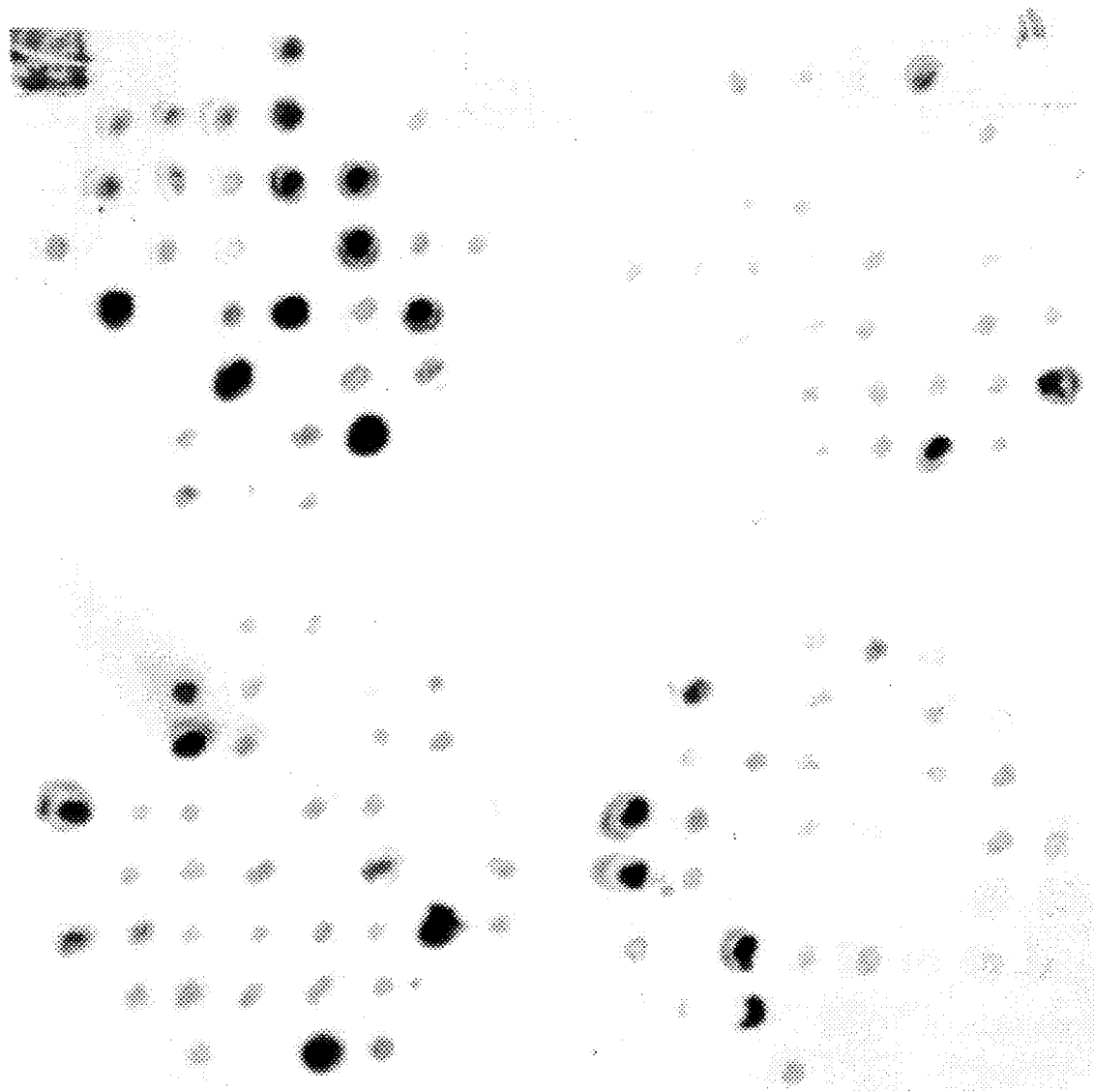
FIG. IIb(I)

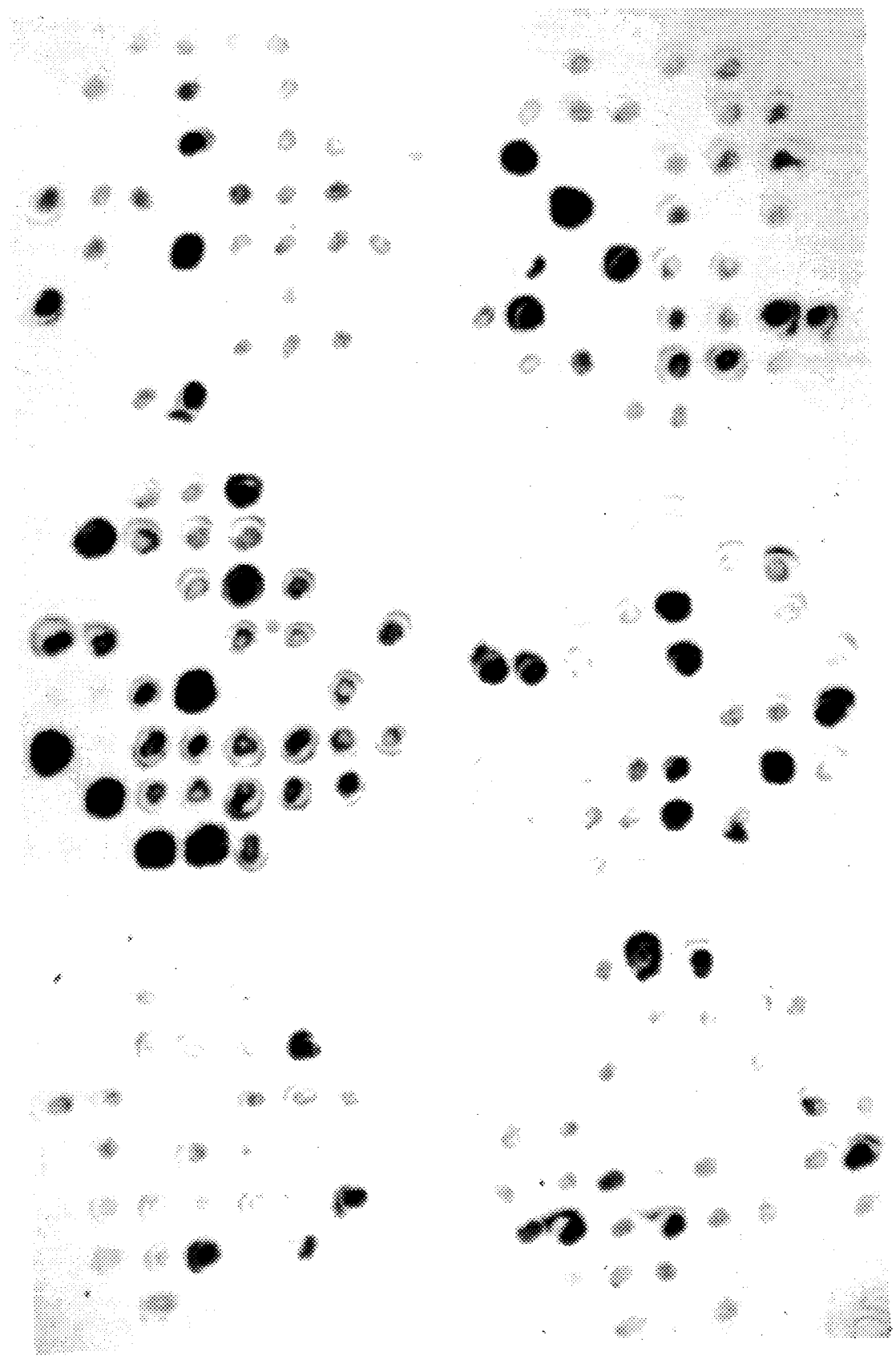
FIG. IIb(2)

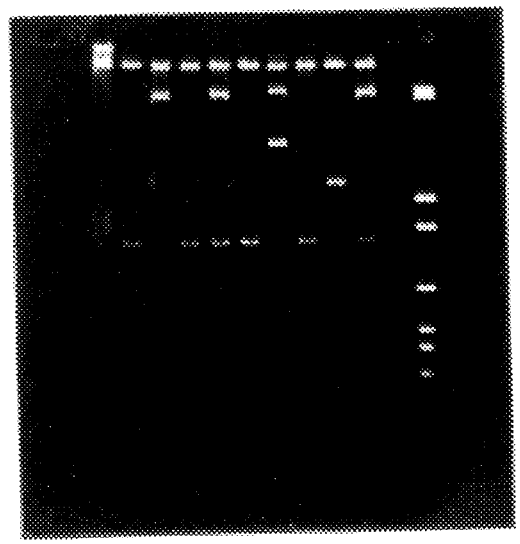
FIG. IIc
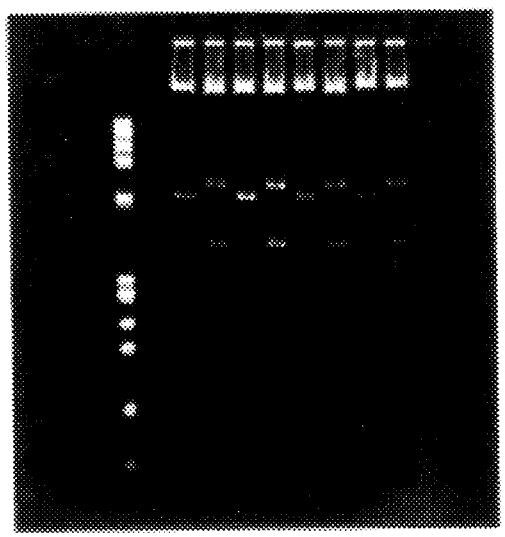
FIG. IId

FIG. 15a
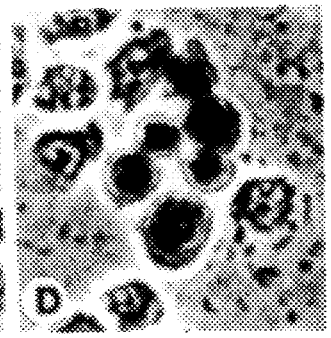
FIG. 15d
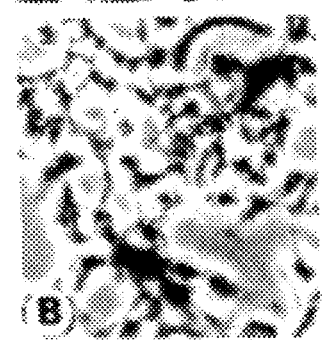
FIG. 15b
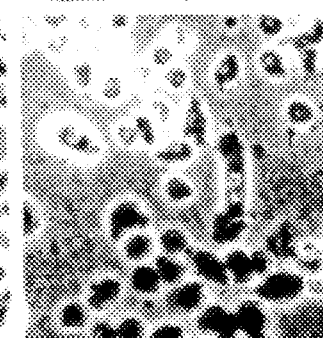
FIG. 15e
FIG. 15c
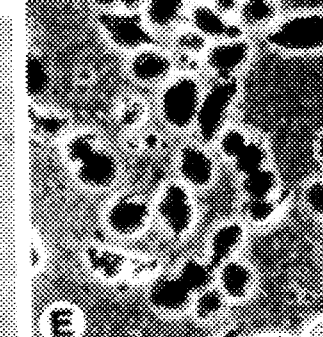
FIG. 15f
FIG. 15g

METHODS AND COMPOSITIONS FOR EXPRESSION OF COMPETENT EUKARYOTIC GENE PRODUCTS

This is a continuation of application Ser. No. 08/008,090, filed on Jan. 22, 1993, which was abandoned upon the filing hereof which was a continuation of application Ser. No. 794,641, filed Nov. 18, 1991, now abandoned, which was a continuation of application Ser. No. 07/423,564, filed Oct. 16, 1989, now abandoned; which was a continuation of application Ser. No. 06/848,657, filed Apr. 4, 1986, now abandoned; which was a continuation-in-part of application Ser. No. 06/626,588, filed Jul. 3, 1984, now abandoned; which is a continuation of application Ser. No. 06/568,176, filed Jan. 5, 1984, now abandoned; which was a continuation-in-part of application Ser. No. 06/504,593, filed Jun. 17, 1983, now abandoned; which was a continuation-in-part of application Ser. No. 06/464,232, filed Feb. 7, 1983, now abandoned.

BACKGROUND OF THE INVENTION

1. Field of the Invention

The industrial production of proteins coded by specific genes such as those encoding hormones, clotting factors, virus proteins, insulin, interferon and others, involves selecting and isolating gene sequences from viral, eukaryotic and other RNA or DNA, splicing of the sequences in the form of DNA into DNA vectors to provide recombinant DNA, and introducing said recombinant DNA into host cells capable of expressing these genes. The vectors may impart to the transformed host cells a phenotypic trait used for isolation and cloning purposes. The gene products are isolated from cell cultures by usual techniques.

Up to now, efforts in this field have usually been based on the adaptation of microorganisms as host cells for expressing genes of interest. Indeed, bacteria are often the organisms of choice since they can be grown rapidly, in large quantities and at low cost. Foreign DNA can be introduced easily into bacterial cells by using vectors such as plasmids, cosmids, viruses and the like.

Use of bacterial hosts, however, is not always sufficient to obtain expression of mature eukaryotic proteins. Many important eukaryotic proteins are modified by glycosylation, acetylation, phosphorylation, specific proteolytic cleavage and other forms of processing. In many instances post-transcriptional and post-translational modifications are crucial in determining the final biological properties of protein products. Non-proteolytic post-translational modifications of certain proteins such as glycosylation, acetylation, phosphorylation and others may not occur correctly, if at all, in bacteria or cell types significantly different from the cell type in which the gene product of interest is normally produced in the organism. The correct form of these modifications may prove critical in the synthesis of fully competent gene products by molecular cloning techniques. For example, when the gene product is a glycoprotein, such as the haemagglutinin of influenza virus, the precise nature of glycosylation may influence the efficiency of antibodies raised against this synthetic protein to protect human beings or animals against influenza virus infections. Moreover, when glycosylation, acetylation or phosphorylation or other modifications are required to stabilize, activate, or mediate intracellular transport or excretion of a protein, the precision of these modifications may be critical to the utility of these genetically engineered protein products in practice.

Because of the above-mentioned shortcomings of using bacteria for the synthesis of complex gene products, there have been a number of attempts to introduce DNA encoding specific eukaryotic proteins into eukaryotic cells. DNA can be introduced by co-transformation into suitable mutant cells which are deficient in the production of a particular enzyme, such a thymidine kinase or hypoxanthine phosphoribosyl transferase. Then by culturing the cells in a selective medium deficient in the enzyme product, transformed cells may be selected for by their ability to grow, i.e., their ability to produce the enzyme. Alternatively, cells can be co-transfected in a positive sense to add a gene that will transduce cells to become selectively resistant to a drug or selective medium such methotrexate, neomycin, or others. Although many of these attempts have enjoyed some measure of success, in most cases the yield of mature gene products has been quite limited.

In order to maximize the yields of expression of fully competent gene products of interest, it would be desirable that the host expression unit system employed consists of an expression vector derived from one cell type or organism that is capable of synthesizing the said fully competent gene products, and that this expression vector directs the synthesis of said gene products in the same or similar cell type or organism as host.

2. Description of the Prior-Art

The heat-shock phenomenon has been studied most extensively in *Drosophila melanogaster*. For a review, see Ashburner and Bonner (1979) Cell 17: 241–254. When Drosophila cells or organs, normally at about 25° C., are exposed to a heat treatment at 35°–37° C., a family of heat-shock genes is activated and most of the genes active at 25° C. are no longer transcribed. Seven genes code for polypeptides with molecular weights between 22,000 and 84,000 daltons. During heat treatment these heat-shock polypeptides are synthesized almost exclusively and after 8 hrs, represent 10% of the total cellular protein [Arrigo, P. (1979) Ph. D. Thesis, University of Geneva]. During heat treatment of Drosphila cells, much of the polysome bound mRNA codes for heat-shock proteins [McKenzie et al. (1975) 72: 1117–1121; Mirault et al. (1978) Cold Spring Harbor Symp. Quant. Biol. 42: 819–827].

All seven Drosophila heat-shock protein genes have been cloned. See, Livak et al. (1978) PNAS 75: 5613–5617; Schedl et al. (1978) Cell 14: 921–929; Craig et al. (1979) Cell 16: 575–588; Holmgren et al. (1979) Cell 18: 1359–1370; Wadsworth et al. (1980) PNAS 77: 2134–2137; Corces et al. (1980) PNAS 77: 5390–5393; Voellmy et al. (1981) Cell 23: 261–270. A number of the genes have been sequenced. See Karch and Torok (1980) Nucleic Acid Res. 8: 3105–3123, and Ingola and Craig (1982) PNAS 79: 2360–2364.

All eukaryotic organisms appear to possess heat shock genes. See Kelly and Schlesinger (1978) Cell 15: 1277–1288. Many of the heat shock genes appear to be conserved throughout widely diverse species, and Drosophila heat shock genes have been shown to be transcribed in mouse cells [Corces et al. (1981) PNAS 78: 7038–7042], frog cells [Voellmy and Rungget (1982) PNAS 79: 1776–1780], and monkey cells [Pelham (1982) Cell 30: 517–528]. Fusion genes consisting of Drosophila heat-shock gene regions and Herpes Simplex virus thymidine kinase gene regions are also transcribed in these heterologous cell systems. No evidence has been presented which would suggest that the protein products of these genes are formed. Pelham, H. and Bienz, M. (1982) p. 43–48 in Heat Shock from Bacteria to Man. Ed. Schlesinger, Ashburner and Tissiéres. Cold Spring Harbour Press. Corces et al. (1982) p.

27–34 in Heat Shock from Bacteria to Man. Ed. Schlesinger, Ashburner and Tissiéres. Cold Spring Harbour Press.

SUMMARY OF THE INVENTION

DNA constructions are provided comprising control elements derived from heat-shock genes associated with genes of interest, which permit the expression of the gene of interest in both procaryotic and eucaryotic cells. In particular, for the efficient synthesis of fully competent gene products, a homologous combination of expression unit and host cell for expression is used and the nature of this homologous system is that of the same or similar cell type or organism that normally produces the said gene product.

BRIEF DESCRIPTION OF THE DRAWINGS

FIG. 2 represents the complete DNA sequence of one strand of the DNA preceding the 70 kdal hsp gene in plasmid 51 except for the white sequences on a black background, which are present in another 70 kdal gene sequence, as determined by the procedure of [Maxam and Gilbert (1977), PNAS 74: 560], and in addition some important restriction sequences as well as the site of the start of transcription and translation (arrows).

FIGS. 3a–3d represent a diagrammatic representation of the procedure for the construction of plasmid pRV15.

In particular, FIG. 3a shows a restriction map of plasmid 51 which after digestion with Sau3A gives rise to an approximately 650 bp fragment referred to henceforth as the 650 bp fragment, one end of which is indicated in detail in FIG. 3c (left part).

FIG. 3b is a restriction map of plasmid pMC1403 which, after restriction with BamHI, leaves one end with the structure indicated in detail in FIG. 3c (right part).

FIG. 3c represents details of the sequence of the ends produced by the restriction digests of plasmids 51 and pMC1403.

FIG. 3d represents the structure of plasmid pRV15 showing the linkage of the Sau3A fragment of plasmid 51 in the BamHI site of plasmid pMC1403. The position of the β-galactosidase gene and of the Drosophila DNA are indicated in the plasmid by heavy lines. Some restriction sites are also indicated.

FIG. 4a is a photograph showing characterization of the structure of plasmid pRV15 indicated in FIG. 3d by the colony hybridization assay of Grunstein and Hogness (1975) PNAS 72: 3961. This was performed using radioactive probes prepared by nick translation [Maniatis et al., (1975) PNAS 72: 1184] of either a 2 kbp XbaI fragment excised from plasmid 132E3 (see FIG. 1a) or a labelled 650 bp Sau3A fragment from plasmid 51 (FIG. 4b). A number of transformants produced using the construction scheme of FIG. 3 were tested as were some colonies of pMC1403 as a control; these colonies are indicated by arrows in FIG. 4a.

FIGS. 5a–5c represents the characterization, by restriction analysis, of the structure for plasmid pRV15 indicated in FIG. 3d. Fragment sized in bps are indicated. In particular:

FIG. 5a is a photograph showing the migration of various DNA fragments under electrophoresis. DNA was prepared from mini-plasmid preparations [Davis et al., (1980), Methods in Enzymoloy, Grossmann and Moldave, eds. 65: 404–414] for plasmid pMC1403, pRV15 and two similar isolates, pRV25 and pRV5. These plasmids were digested with restriction enzymes as indicated below and the fragments of DNA produced were electrophoresed on 0.85% agarose gels at 150 v for 4 hours after which bands were visualized using ethidium bromide staining and U.V. photography. Identification of the lanes is as follows:

| Lane | | |
|---|---|---|
| 1 | pMC1403 | - Sau3A/XhoI |
| 2 | " | - SalI/XbaI |
| 3 | " | - SalI/EcoRI |
| 4 | pRV25 | - SalI/XhoI |
| 5 | " | - SalI/XbaI |
| 6 | " | - SalI/EcoRI |
| 7 | pRV15 | - SalI/XhoI |
| 8 | " | - SalI/XbaI |
| 9 | " | - SalI/EcoRI |
| 10 | pRV5 | - SalI/XhoI |
| 11 | " | - SalI/XbaI |
| 12 | " | - SalI/EcoRI |

FIG. 5b is similar to FIG. 5a for a series of digests and analyses performed identically. The lanes are as follows:

| Lane | | |
|---|---|---|
| 1 | pRV15 | - XhoI |
| 2 | " | - XbaI |
| 3 | " | - SalI/XhoI |
| 4 | " | - SalI/XbaI |
| 5 | " | - SalI |
| 6 | pRV5 | - XhoI |
| 7 | " | - XbaI |
| 8 | " | - SalI/XhoI |
| 9 | " | - SalI/XbaI |
| 10 | " | - SalI |

FIG. 5c is similar to FIGS. 5a and 5b and concerns restriction digests and analyses performed for fragments separated on gels of 5% polyacrylamid. Electrophoresis was at 40 v for 14 hours.

| Lane | 1 | 51 | - Sau3A/XbaI |
|---|---|---|---|
| | 2 | 51 | - Sau3A/XhoI |
| | 3 | 51 | - Sau3A |
| | 4 | pMC1403 | - Sau3A |
| | 5 | pRV15 | - Sau3A/XbaI |
| | 6 | pRV15 | - Sau3A/XhoI |
| | 7 | pRV15 | - Sau3A |
| | 8 | Diagrammatic representation of 51 - Sau3A | |
| | 9 | Diagrammatic representation of pBR322 Sau3A | |

Figure 6A:
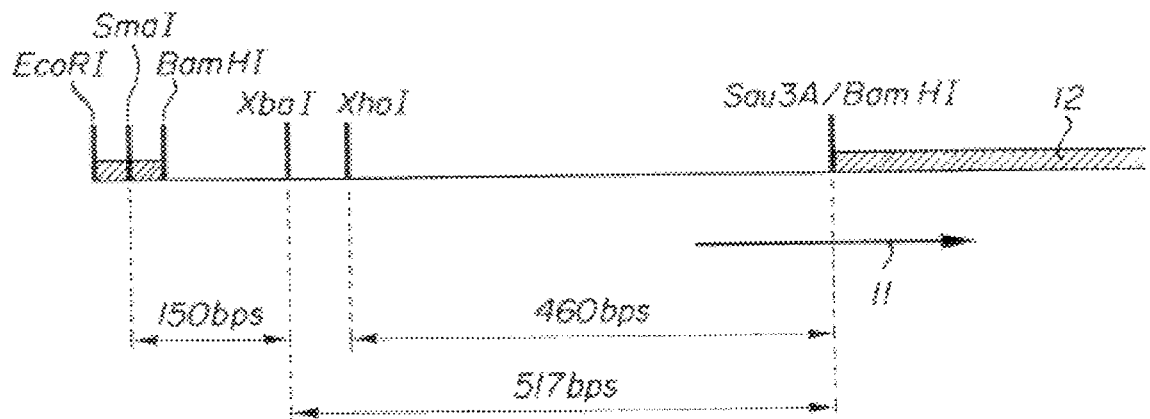
Figure 6B:
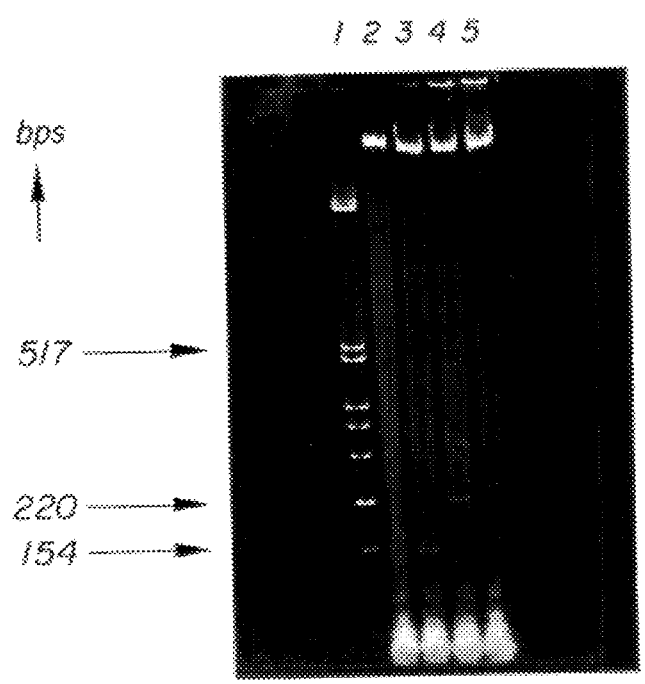

FIGS. 6a–6b refer to an analysis of the orientation of the Drosophila 70 kdal hsp gene Sau3A fragment in plasmid pRV15. In particular:

FIG. 6a is a diagrammatic representation of the sizes of predicted restriction fragments that would result if the desired orientation of Drosophila elements and the E. coli β-galactosidase gene is indeed the case in plasmid pRV15.

FIG. 6b is a photograph of an acrylamide gel (5%) analysis of the results of restriction of plasmid pRV15 and pBR322 to test the prediction presented in the diagram of FIG. 6a. Analyses were performed as described for the cases represented by FIG. 5c.

| Lane | 1 | pBR322 | - HinfI |
|---|---|---|---|
| | 2 | pRV15 | - EcoRI |
| | 3 | pRV15 | - XbaI/EcoRI |
| | 4 | pRV15 | - XhoI/EcoRI |
| | 5 | pRV15 | - XhoI |

The position of bands of sizes 517, 220 and 154 bps are indicated by arrows and are derived from the known sizes of fragments derived by restriction of plasmid pBR322 by HinfI.

FIGS. 7a–7e, which show plasmids or fragments of plasmids after digestion with restriction enzymes, represent schematically the construction of plasmid 520, which consists of incorporating the SamI-SalI fragment of pRV15 containing the lac operon fragment and the Drososphila 650 bp control element into plasmid pSVod using the BamHI-SalI restriction site. In particular:

FIG. 7a represents pRV15, FIG. 7c represents pSVod; FIG. 7b represents a SmaI-SalI fragment of pRV15; FIG. 7d represents pSVod after excision of a BamHI-SalI fragment; and FIG. 7e represents p520.

Figure 8A:
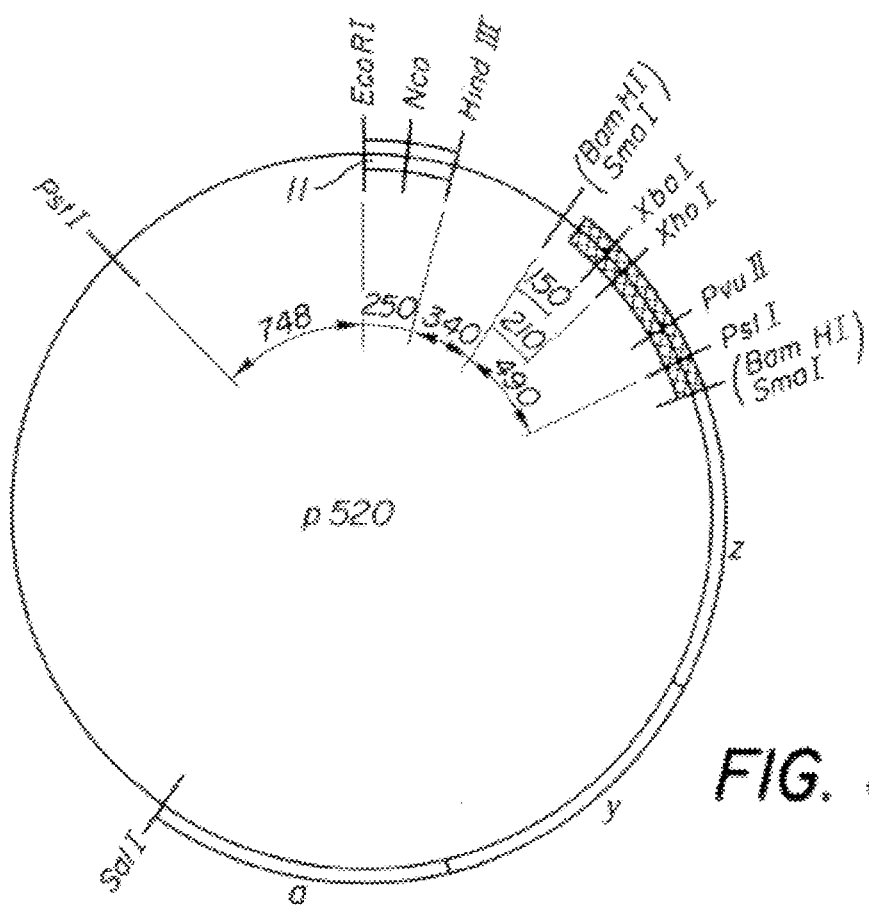

FIG. 8a is a restriction map for plasmid vector 520 indicating the position of selected restriction sites in the structure of the plasmid.

Figure 8B:
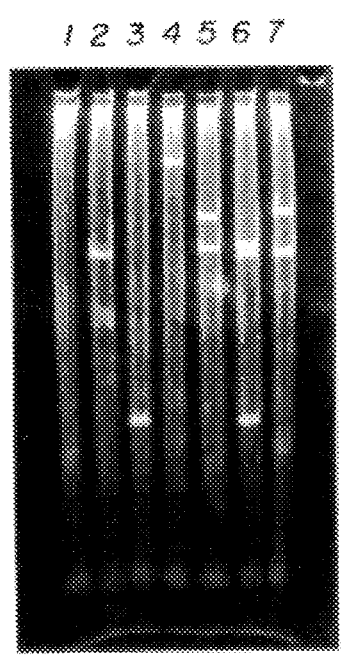

FIG. 8b is a photograph of an agarose gel analysis of restriction enzyme digestions of plasmid 520 performed as described in the case of pRV15 (see FIG. 5a).

| Lane | 1 | - HindIII |
|---|---|---|
| | 2 | - XhoI/EcoRI |
| | 3 | - HindIII/EcoRI |
| | 4 | - PstI |
| | 5 | - HindIII/PstI |
| | 6 | - PstI/HindIII/EcoRI |
| | 7 | - PstI/EcoRI |

Figure 8C:
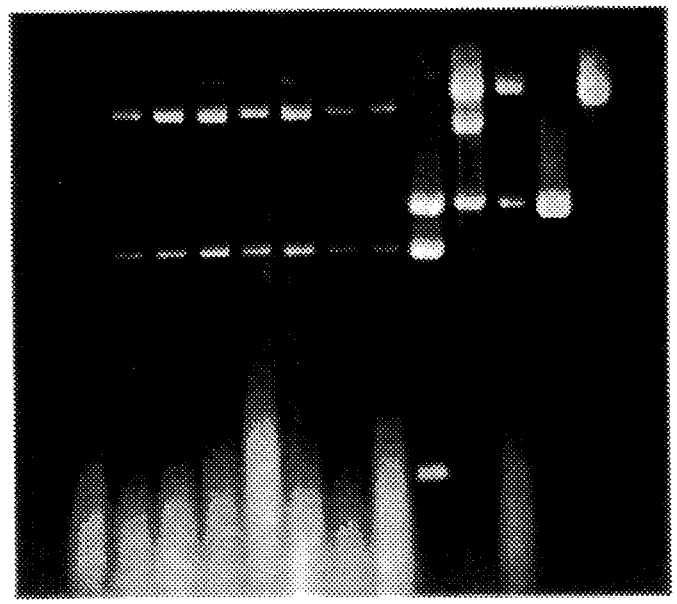

FIG. 8c is a photograph also referring to the characterization of plasmid 520. It shows agarose gel analysis of various restriction digest of plasmids pSVod, pRV15 and 520-like plasmids, i.e., plasmids 639, 520, 519, X, Y, Z.

| Lane | 1 | 639 | - SalI/EcoRI |
|---|---|---|---|
| | 2 | 520 | - " |
| | 3 | 519 | - " |
| | 4 | 516 | - " |
| | 5 | X | - " |
| | 6 | Y | - " |
| | 7 | Z | - " |
| | 8 | pSVod | - " |
| | 9 | pRV15 | - " |
| | 10 | pSVod | - XhoI/EcoRI |
| | 11 | pRV15 | - " |

Note that the digests in Lanes 8 and 9 are incomplete.

Figure 8D:
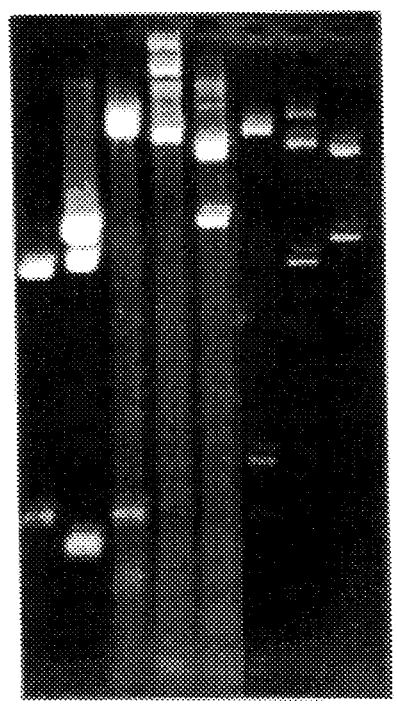

FIG. 8d is a photograph showing further restriction digests of plasmid 520 by comparison with digests of plasmids pSVod and pRV15.

| Lane | 1 | pSVod | - PstI/EcoRI |
|---|---|---|---|
| | 2 | pSVod | - HindIII/SalI |
| | 3 | pRV15 | - PstI/EcoRI |
| | 4 | pRV15 | - HindIII/SalI |
| | 5 | pRV15 | - SalI/XbaI |
| | 6 | 520 | - PstI/EcoRI |
| | 7 | 520 | - HindIII/SalI |
| | 8 | 520 | - SalI/XbaI |

Note that the digests in Lanes 2 and 7 are incomplete.

Figure 9A:
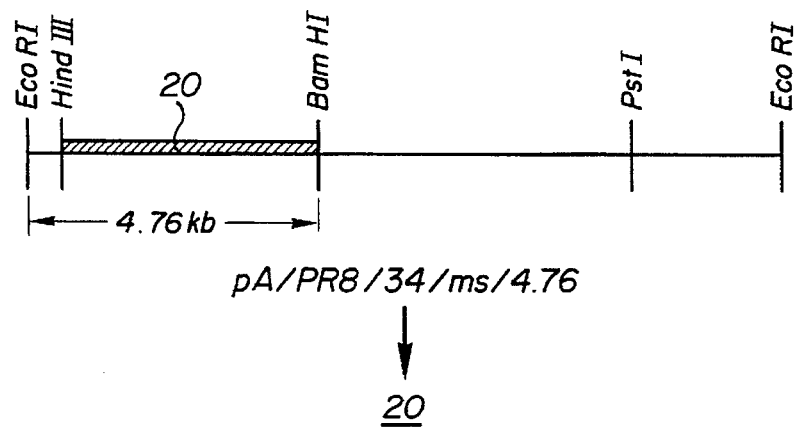
Figure 9B:
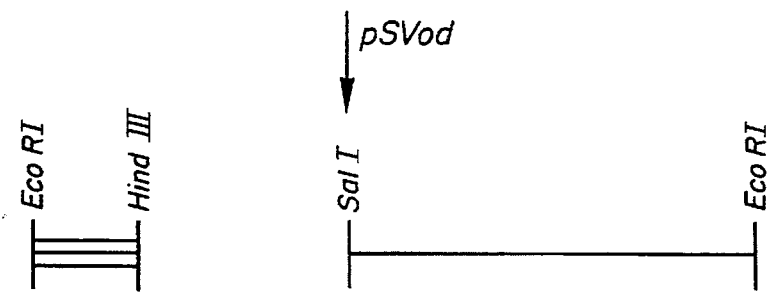
Figure 9C:
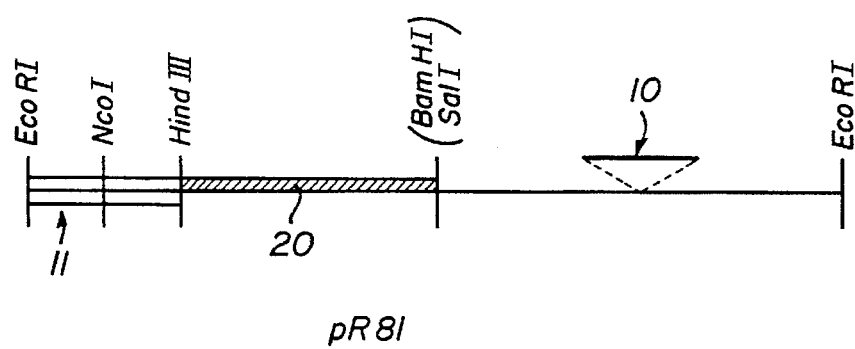

FIGS. 9a–9c refer to the construction of plasmid PR81. In particular:

FIG. 9a represents the Mount Sinai A/PR 8/ms/4.76 plasmid from which a fragment (ref. no. 20) was excised with BamHI and HindIII; FIG. 9b represents pSVod less a HindIII-SalI fragment; and FIG. 9c represents plasmid PR81, i.e., the ligation product of the BamHI-HindIII fragment 20 with a SalI-HindIII digest.

Figure 9D:
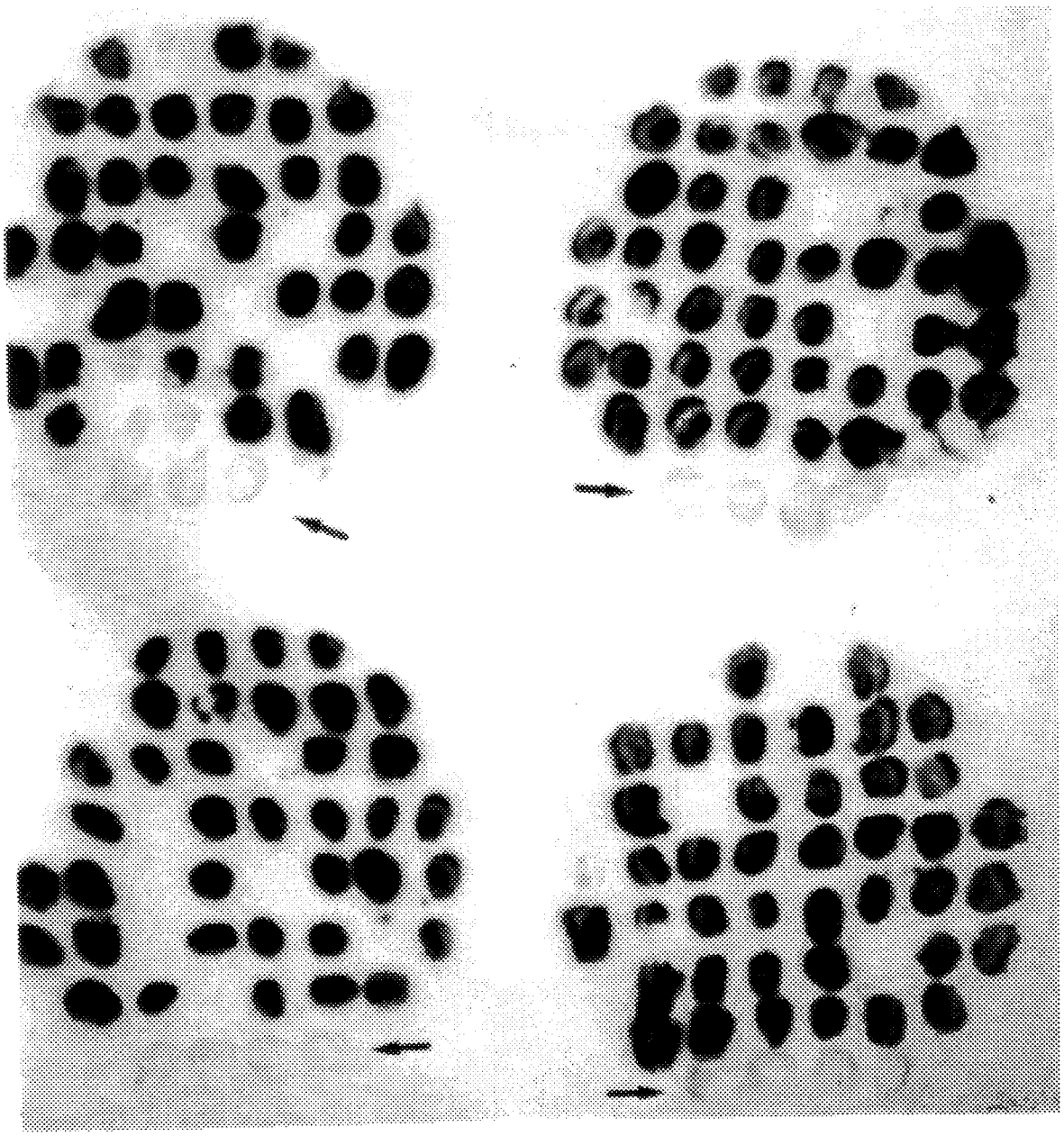
Figure 9E:
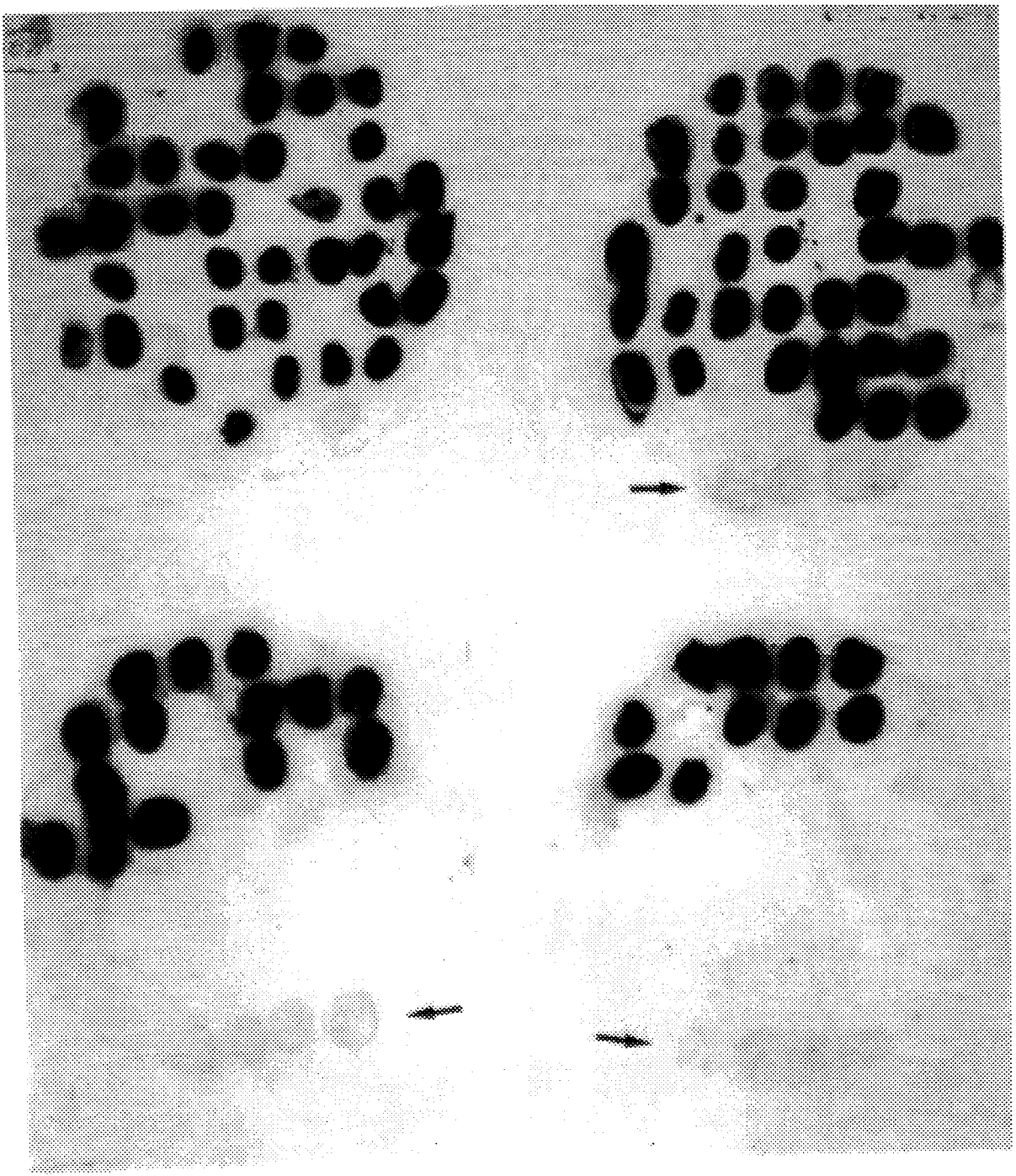

FIGS. 9d and 9e are photographs of a Grunstein colony hybridization analysis of PR81-like plasmids, performed as described for pRV15 (see FIG. 4). The nick-translated probe used was the BamHI/HindIII fragment for A/PR 8/ms/4.76. As a control some pSVod containing colonies are indicated by the arrows.

Figure 9F:
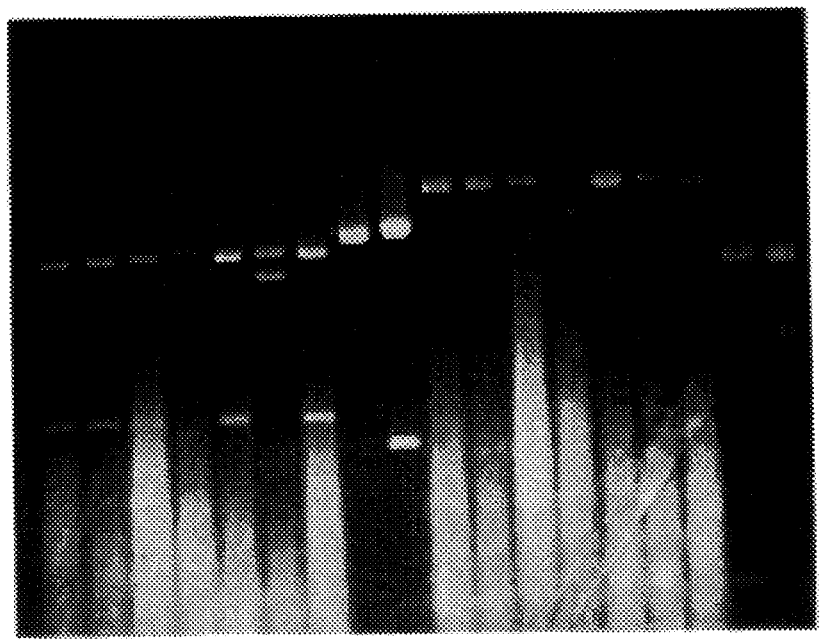

FIG. 9f is a photograph of a restriction analysis of PR81-like plasmids shown by colony hybridization analysis in FIGS. 9d and 9e.

| Lane | 1 | filter | 21, Sample 30 | - | EcoRI |
|---|---|---|---|---|---|
| | 2 | " | 21, Sample 44 | - | " |
| | 3 | " | 22, Sample 11 | - | " |
| | 4 | " | 22, Sample 24 | - | " |
| | 5 | " | 23, Sample 10 | - | " |
| | 6 | " | 23, Sample 31 | - | " |
| | 7 | " | 24, Sample 8 | - | " |
| | 8 | pSVod | | - | " |
| | 9 | PR 8/ms/4.76 | | - | " |
| | 10 | filter | 21, Sample 30 | - | HindIII/SalI |
| | 11 | " | 21, Sample 44 | - | " |
| | 12 | " | 22, Sample 11 | - | " |
| | 13 | " | 22, Sample 24 | - | " |
| | 14 | " | 23, Sample 10 | - | " |
| | 15 | " | 23, Sample 31 | - | " |
| | 16 | " | 24, Sample 8 | - | " |
| | 17 | pSVod | | - | " |
| | 18 | PR 8/ms/4.76 | - | | " |

Figure 10A:
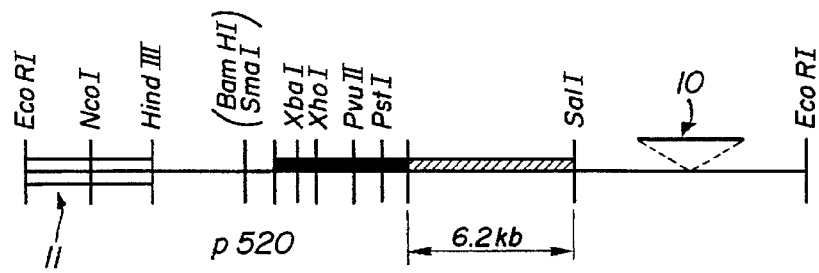
Figure 10B:
Figure 10C:
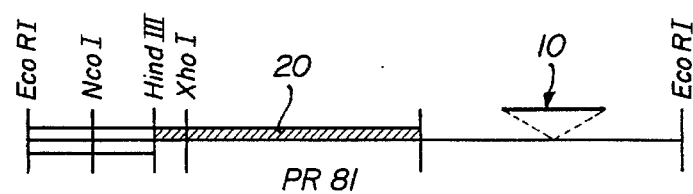
Figure 10D:
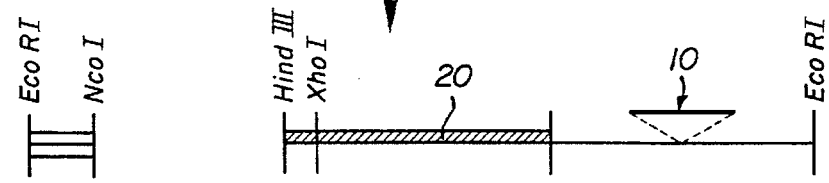
Figure 10E:
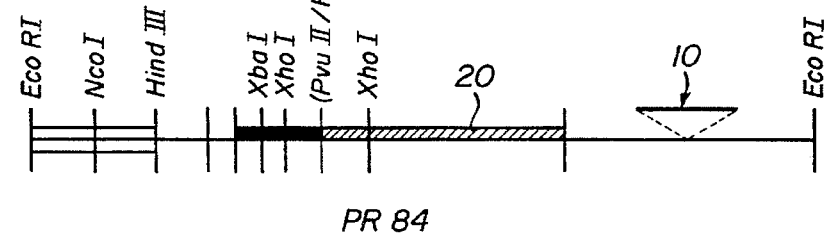

FIGS. 10a–10e refer to the construction scheme of plasmid PR84. This plasmid was constructed as shown in the figure and consists of substituting the haemagglutinin (HA) gene 20 present in plasmid PR81 for the β-galactosidase gene in plasmid 520. In particular:

FIG. 10a represents plasmid 520; FIG. 10c represents plasmid PR81; FIG. 10b represents an NcoI-PvuII fragment excised from 520; FIG. 10d represents PR81 after digestion with HindIII and NcoI; FIG. 10e represents schematically PR84.

Figure 10F:

FIG. 10f is a more detailed representation of PR84 with one strand of base-pairs including the sequence originating from PR 8/ms; only the crucial joining region between the Drosophila HS control element and the HA start sequence is detailed.

FIGS. 11a, 11b(1), 11b(2), 11c, and 11d refer to checking the results from the construction of PR84. FIG. 11a is a photograph referring to the restriction digestion of plasmids PR81, PR 8/ms/34, pSVod and 520.

| Lane | 1 | PR81 | - HindIII/EcoRI |
|---|---|---|---|
| | 2 | PR81 | - XhoI/EcoRI |
| | 3 | PR81 | - NcoI |

| | | |
|---|---|---|
| 4 | PR81 | - NcoI/XhoI |
| 5 | PR 8/ms/34 | - HindIII/EcoRI |
| 6 | PR 8/ms/34 | - XhoI/EcoRI |
| 7 | PR 8/ms/34 | - NcoI |
| 8 | PR 8/ms/34 | - NcoI/XhoI |
| 9 | pSVod | - NcoI/SalI |
| 10 | pSVod | - PvuII/SalI |
| 11 | pSVod | - HindIII/EcoRI |
| 12 | pSVod | - HinfI STANDARD |
| 13 | 520 | - PvuII |
| 14 | 520 | - PvuII/XbaI |
| 15 | 520 | - PvuII/XhoI |
| 16 | 520 | - PvuII/EcoRI |
| 17 | 520 | - PvuII/NcoI |
| 18 | 520 | - NcoI |
| 19 | 520 | - NcoI/XbaI |
| 20 | 520 | - NcoI/XhoI |

FIGS. 11b(1) and 11b(2) refer to a Grunstein colony hybridization analysis of PR 84-like plasmids. A nick-translated radioactive probe (approximately $10^8$ cpm/μg) of the plasmid 51 Sau 3A/XhoI Drosophila control element fragment was used in these assays.

FIG. 11c refers to a 5% polyacrylamide gel analysis of the XhoI digestion products of PR84-like plasmids selected from the positive colonies identified in FIG. 11b.

| Lane | | filter | 3, | Sample | 12 | | - XhoI |
|---|---|---|---|---|---|---|---|
| | 2 | " | 3, | " | 15 | (PR82) | - " |
| | 3 | " | 3, | " | 22 | " | - " |
| | 4 | " | 3, | " | 42 | (PR84) | - " |
| | 5 | " | 3, | " | 45 | " | - " |
| | 6 | " | 4, | " | 19 | " | - " |
| | 7 | " | 4, | " | 40 | " | - " |
| | 8 | " | 5, | " | 16 | " | - " |
| | 9 | " | 5, | " | 28 | " | - " |
| | 10 | " | 5, | " | 39 | " | - " |
| | 11 | pSVod | | | | | - HinfI STANDARD |

FIG. 11d refers to further restriction analysis of plasmids giving the XhoI digestion pattern shown in Lanes 2, 4, 6 and 8 of FIG. 11c. Analysis was performed as described for FIG. 11c.

| Lane | 1 | φ × 174 RF | | | | - HaeIII STANDARD |
|---|---|---|---|---|---|---|
| | 2 | filter | 5, | Sample | 16 | - XbaI/NcoI |
| | 3 | " | 5, | " | 16 | - XhoI/NcoI |
| | 4 | " | 4, | " | 19 | - XbaI/NcoI |
| | 5 | " | 4, | " | 19 | - XhoI/NcoI |
| | 6 | " | 3, | " | 42 | - XbaI/NcoI |
| | 7 | " | 3, | " | 42 | - XhoI/NcoI |
| | 8 | " | 3, | " | 15 | - XbaI/NcoI |
| | 9 | " | 3, | " | 15 | - XhoI/NcoI |

FIGS. 12a, 12b, 12c, and 12d describe the characterization of plasmid p629.

Figure 12A:
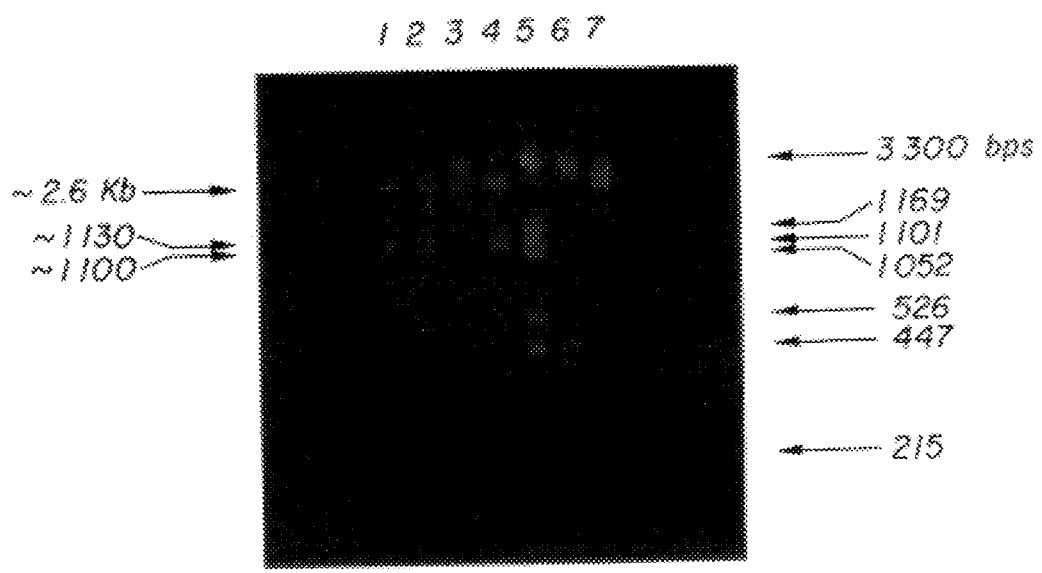

FIG. 12a refers to a 5% polyacrylamide gel analysis of some candidate 629 series plasmids.

| | Plasmid | |
|---|---|---|
| Lane 1 | 629/8 | BglII/EcoRI |
| 2 | 629/7 | " |
| 3 | 629/6 | " |
| 4 | 629/4 | " |
| 5 | DNA standard | |

Figure 12B:
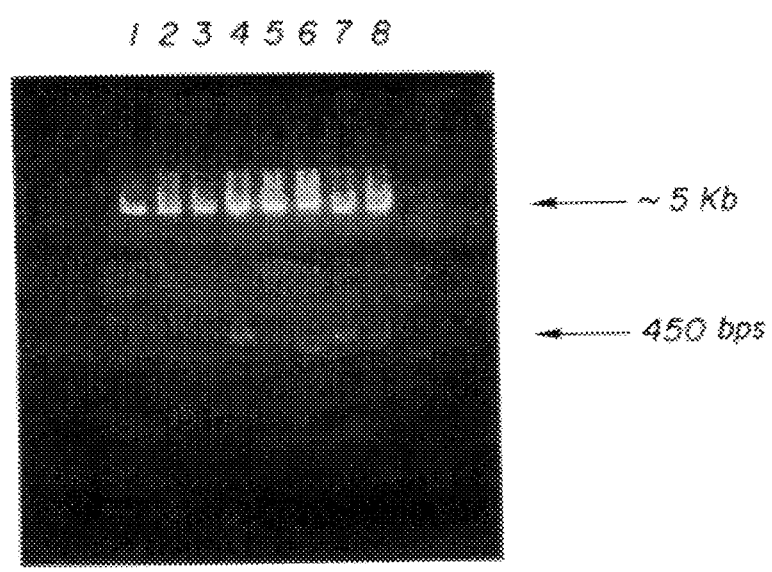

FIG. 12b refers to another 5% polyacrylamide gel analysis of all eight candidate 629 series plasmids.

| | Plasmid | |
|---|---|---|
| Lane 1 | 629/1 | XhoI |
| 2 | 629/2 | " |
| 3 | 629/3 | " |
| 4 | 629/4 | " |
| 5 | 629/5 | " |
| 6 | 629/6 | " |
| 7 | 629/7 | " |
| 8 | 629/8 | " |

Figure 12C:
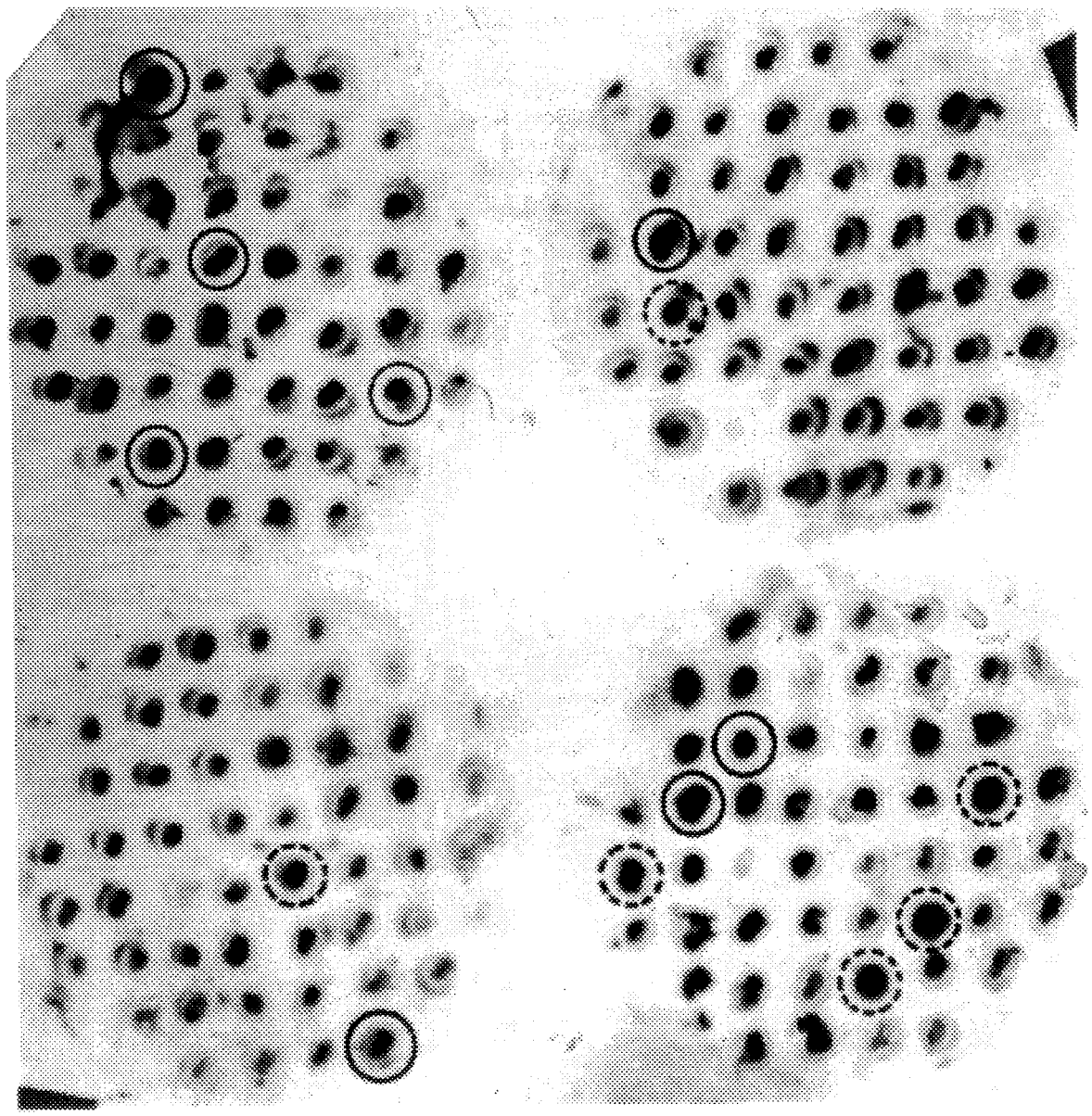

FIG. 12c shows a Grunstein colony hybridization assay using the nick-translated Xho-BglII fragment from plasmid p622b.

Figure 12D:
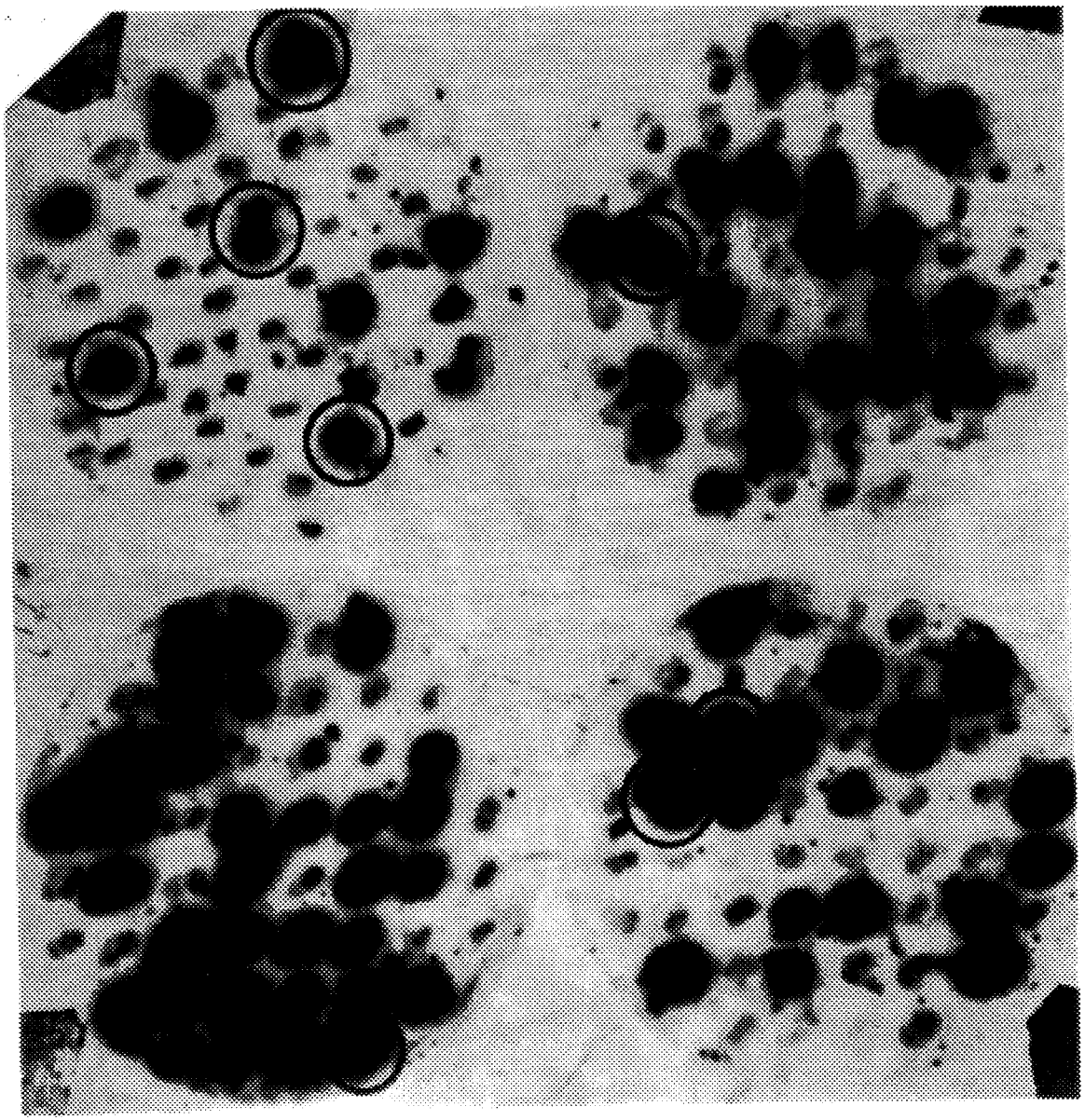

FIG. 12d shows a Grunstein colony hybridization assay using the nick-translated HindIII/BamHI.HA gene fragment from plasmid A/PR 8/mx/34.

Figure 13:
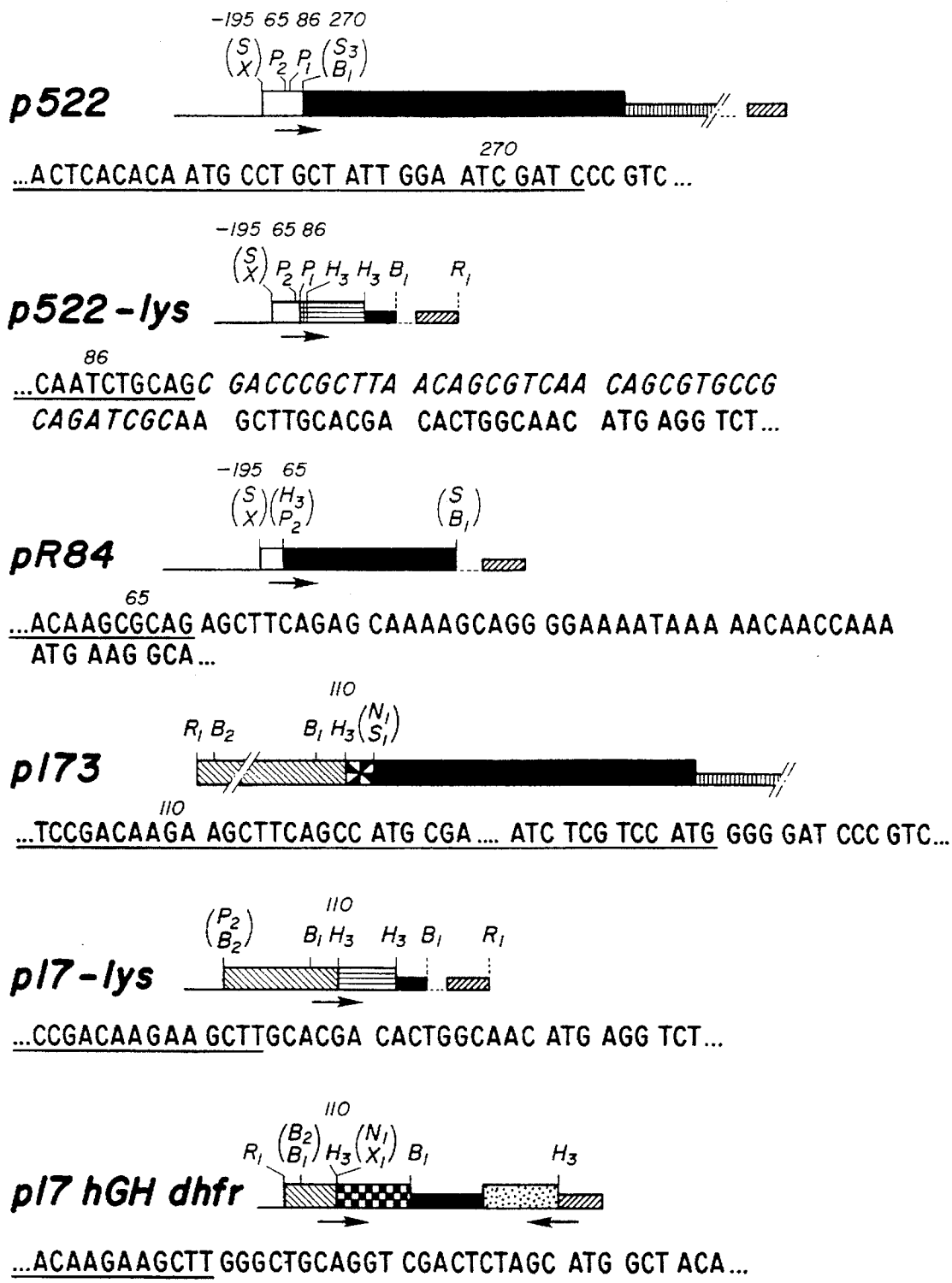

FIG. 13 relates to Example 3 herein and depicts heat-shock hybrid gene constructs. Symbols used: D.melanogaster hsp70 gene promoter regions 1 ▭; E. coli β-galactosidase-coding sequence ▬; D.melanogaster hsp70 gene 3'trailer sequence 3 ▨; thymidine kinase gene RNA leader sequence ▦; chicken lysozyme gene 5 ▬; SV40 origin of replication 6 ▨; SV40 gene 3 'trailer sequences 7 ▨; human Haemagglutinin gene 8 ▨; human hsp70 gene promoter regions 9 ▨; human hsp70-coding region 10 ▨; human growth hormone gene 11 ▨; dihydrofolate reductase gene 12 ▨. Hsp70 gene sequences are underlined, the transcriptional orientation of the hybrid genes is indicated by arrows, B1: BamH1; B2: BglIII; H3: HindIII; Ni: NcoI; P1: PstI; P2: PvuII; R1: EcoR1; S: SalI; S1: SmaI; S3: Sau3A; X: XhoI; X1: XbaI. The length of the -galactosidase-coding region is 3 kb.

Figure 14:
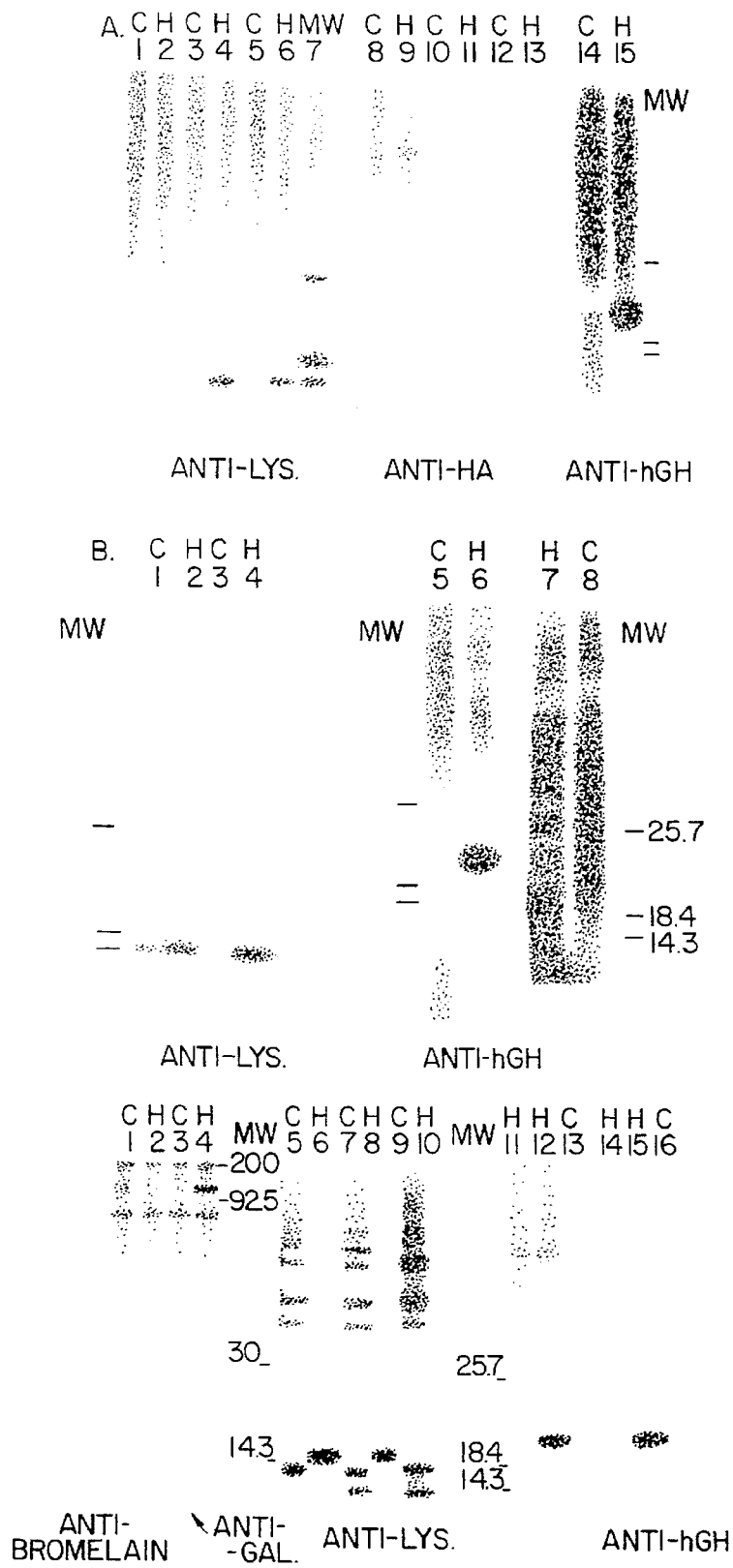

FIG. 14 relates to Example 3 herein and depicts electrophoretio analysis of hybrid gene products synthesized by heat-treated (H) or untreated (C) Xenopus oocytes. A. Examination of cytoplasmic extracts prepared from oocytes that had been injected with pR84 (Lanes 1,2,8 and 9), p17-lys (Lanes 3,4,10 and 11), p522-lys (Lanes 5,6,12 and 13) or p17hGH dhfr DNA (Lanes 14 and 15). Electrophoresis was carried out following immunoprecipitation with the antisera indicated in the FIG. B. Anlysis of medium samples from oocytes containing p17-lys (Lanes 1 and 2), p522-lys (Lanes 3 and 4) or p17hGH dhfr DNA (Lanes 5 to 8). The samples were either directly used for electrophoresis (Lanes 7 and 8) or following immunoprecipitation with the antisera indicated in the Figure (Lanes 1 to 6).

FIG. 15 relates to Example 3 herein and depicts hybrid gene products made by heat-treated (H) or untreated (C) transfected COS 1 (Lanes 1 to 13) or CHO (Lanes 14 to 16) cells. Cells had been transfected with p522 (Lanes 1,2,3,4,9 and 10), p522-lys (Lanes 5 and 6), p17-lys (Lanes 7,8,11 and 14) or p17hGH dhfr DNA (Lanes 12,13,15 and 16). Cytoplasmic extracts from p522-containing cells were analysed by electrophoresis following immunoprecipitation with either anti-bromelain or anti-galactosidase antisera (Lanes 1 to 4). Lanes 5 to 16 show immunoprecipitated proteins from media samples.

DESCRIPTION OF THE SPECIFIC EMBODIMENTS

Methods and compositions are provided for the controlled expression of a gene in a eukaryotic host. The present invention is particularly useful for expressing mammalian genes in mammalian hosts, typically in a host cell culture similar or identical to the host in which the gene is naturally expressed. In this way, post-transcriptional and post-translational modifications of the gene products will be achieved, thus assuring the competence of such resulting gene products.

DNA sequences which comprise an inducible expression control region derived from a eukaryotic heat-shock protein (hsp) gene are employed. Such control regions are inducible for example by elevated temperatures and include sequences responsible for both transcriptional and translational control of the hsp gene activity, e.g., the promoter region (RNA polymerase recognition and binding sites), and possibly also heat-shock protein gene control sequences which have been modified in such a way that they allow the constitutive expression of downstream coding sequences. The control region may also include other portions of the translated and untranslated regions of the hsp gene which participate in transcriptional and/or translational regulation including 3' untranslated sequences. Furthermore, sequences derived from the 3' untranslated region flanking the structural gene (i.e., the noncoding portion of the gene of interest) may be included. Conveniently, the entire hsp gene including the structural region as well as the 5' and 3 ' flanking regions may be employed. In the latter case, the gene of interest may be inserted internal to the structural region to produce a fused protein upon translation. The protein of interest may then be recovered by conventional means.

The term heat-shock protein (hsp) gene will be employed in the specification and the claims to denote the entire gene locus responsible for the inducible expression of heat-shock proteins, specifically including the 5' regulatory sequences upstream of the structural region, the structural reigon which encodes the mRNA transcript (including untranslated leader sequences) and the 3' flanking region downstream of the structural gene.

Heat-shock protein genes may be obtained from most higher eukaryotic organisms. Particular heat-shock proteins have been identified in fruit flies (Drosophila), mice, frogs, monkeys, and man. Heat-shock genes suitable as a source for the control regions of the present invention may be obtained from any of these or other eukaryotic organisms. Although heat-shock genes drived from one species can be expressed in other species and even in procaryotes, it is generally desirable that in order to optimize the expression advantages of heat-shock control elements at both the transcriptional and the translational levels, these elements should be derived from the same or similar organism or cell type that will be used for expression of the gene of commercial interest. For instance, constructions including genes under control of Drosophila heat-shock elements can be most advantageously expressed in prosophila cells in culture.

In the Experimental section hereinafter, an inducible expression control region obtained from a heat-shock protein gene which encodes for a 70 kdal heat-shock protein found in Drosophila was used to express *E. coli* β-galactosidase gene in *E. coli*, COS I Monkey cells, and in Xenopus occytes. The same region was used to control the expression of the influenza haemagglutinin gene in COS I cells.

The inducible expression control region of the present invention may be combined with an extrachromosomal replication system for a predetermine host to provide an expression vector for that host. Such vectors will include DNA sequences having restriction site(s) for insertion of gene(s) 3' to said control regions to provide the regulated transcription and translation of the inserted genes. The vector can also include markers for selection in bacteria and in eukaryotic host cells, a prokaryotic replication system allowing cloning of the vector in a prokaryotic host, and other DNA regions of interest.

Alternatively, the expression control region can be joined to a desired structural gene and the resulting DNA constructs introduced directly into the host cells. Methods for such direct transfer include injection of the DNA into nuclei [Cappechi (1980) cell 22: 479–488] and co-transformation by calcium phosphate precipitation [Wigler et al. (1979) Cell 16: 777–785] or DEAE dextran [McCutchan, J. H. and Pagano J. S. (1968) J. Nat. Cancer Inst. 41: 351–357].

As stated above, the DNA constructs of the present invention may include differing portions of the hsp gene. The constructs will include at least the 5' regulatory region which carries the promoter, regulatory sequences such as operators, activators, cap signals, signals enhancing ribosomal binding, and other sequences as well as additional DNA leader sequences responsible for transcriptional and translational control. The DNA constructs may also include part of the protein coding sequence of the hsp gene, resulting in the production of fused proteins when the foreign gene to be expressed is inserted downstream of the hsp sequences. If a fused protein is not desired, it will be necessary to remove the hsp coding sequences from the isolated hsp DNA by usual methods such as restriction by enzymes and exonuclease digestion.

It may be desirable to leave at least a portion of the hsp structural gene downstream from the natural translational initiation codon. In this way, a fused protein including the amino-terminal amino acid sequences of the heat-shock protein is provided. When such fused proteins are produced, it may be desirable to introduce selective cleavage sites so that the desired protein can be separated from the precusor protein. See Riggs U.S. Pat. No. 4,366,246 which teaches how such cleavage sites may be introduced.

The expression control region of the present invention will usually be combined with a terminator for complete transcriptional control of the inserted structural gene. Conveniently, the terminator can be derived from the heat-shock gene itself, although the inserted structural gene may carry its own or any other suitable terminator sequence.

Extrachromosomal replication systems may also be used. Suitable replication systems include autonomously replicating sequences as described by Struhl et al. 9(1979) PNAS 73: 1471–1475 and the 2 μm plasmid for replication in yeast. Mammalian replication systems could be derived from papovaviruses, such as simian virus 40 and bovine papilloma virus; adenoviruses; avian retroviruses, such as arian sarcoma virus; and mammalian retroviruses such as Moloney leukemia virus.

In addition to the optional eukaryotic replication system, it is advantageous to provide a prokaryotic replication system to allow for cloning of the vector in a bacterial host. This allows large quantities of the vector to be grown in well characterized bacterial systems prior to transforming a eukaryotic host. Suitable prokaryotic replication systems are well known and include plasmids such as pBR322, pRK290, ColE1, and bacteriophages, e.g. λdv. The prokaryotic replication systems will necessarily include an origin of replication recognizable by a prokaryotic host, and will usually include one or more markers for the selection of transformants in the prokaryotic host. Such markers include biocide resistance, toxin resistance, and the like. Alternatively, complementation allowing the growth of an auxotrophic host in a selective medium may be employed. Such techniques are well known in the art and need not be described further.

Usually, the markers employed will be different for selection in prokaryotic and eukaryotic hosts. Various dominantly acting markers are useful in selecting for transformed mammalian cell lines. They usually comprise a specific gene whose expression confers a new drug-resistant phenotype to the mammalian cells in an appropriate selective medium. Specific markers include the bacterial xanthine-guanine phosphoribosyl transferase gene which can be selected in medium containing mycophenolic acid and xanthine [Mulligan et al. (1981) PNAS 78: 2072–2076]; transformants with vectors carrying a mouse cDNA fragment coding for dihydrofolate reductase may be selected for using medium containing aminopterin [Subramani et al. (1981) Mol. Cell Biol. 1: 854–861]; and a bacterial plasmid gene specifying an amino-glycoside phosphotransferase that inactivates the anti-bacterial action of neomycin-kanamycin derivatives may be selected for using medium containing G418 a neomycin derivative toxic for most mammalian cell lines [Colbere-Garapin et al. (1981) J. Mol. Biol. 150: 1–14].

It is evident that the number of copies of gene expression units introduced into a host cell may vary and that by proximal combination of one of the amplifiable genes such as the mouse dihydrofolate reductase gene the number of copies of integrated gene expression units may likewise be amplified by induction of the amplification of the associated amplifiable gene and the proximal DNA. See for example the co-amplification of dihydrofolate reductase cDNA and the $E.$ $coli$ XGPRT (xanthine-guanine phorphoribosyl transferase) gene in Chinese ovary cells [Rungold, G. et al. (1981). J. Mol. and Appl. Genetics, 1, 165–175].

In the exemplary method for preparing the vectors of the subject invention, both the expression control region of the heat-shock protein gene and the eukaryotic replication system are inserted into a suitable prokaryotic plasmid. The manner and order of the insertion are not critical, and it is necessary only that the resulting vector retains viable replication systems for prokaryotic and when necessary eukaryotic hosts.

The DNA constructs containing Drosophila heat-shock gene control segments functionally linked to a structural gene of interest can be used to synthesize products of said gene in Drosophila cells or cultured cells closely related to Drosophila. Since the structural gene is under the transcription and if necessary translation control of the heat-shock control element, its expression can be enhanced by for example increasing the ambient temperature of the cells for instance in the range 37°–42° C. By such induction a large fraction of the newly made mRNA will be derived from said structural gene. Now if the structural gene is a human gene encoding a protein requiring complex processing, the expression vector preferably comprises, in addition to said structural gene, replication elements and marker genes, a heat-shock control element derived from a human heat-shock gene. This construct will be introduced advantageously into cultured human cells by procedures described above to produce products of said human gene. As necessary the choice of recipient human cells will be made on the basis of their competence in correctly expressing the fully processed gene product.

A wide variety of structural genes may be introduced into the subject vectors to permit the production of various gene products including polypeptides, such as enzymes, proteins, hormones, novel protein structures, and the like.

Experimental

The following examples are offered by way of illustration.

1. The construction of plasmid pRV15 which contains the $E.$ $coli$ β-galactosidase gene under the control of a Drosophila heat-shock control element A 650 base pair (bp) DNA fragment from one of the two Drosophila 70 kdal heat-shock protein genes, containing a heat-shock gene transcription control element, a complete RNA leader sequence, a translation initiation signal and a sequence coding for the first few amino acids of the Drosophila 70 kdal heat-shock protein, was obtained from a sub-clone of part of plasmid 132E3 [Schedl et al. (1978) Cell 14: 921–929; see FIG. 1]. Plasmid 132E3 contains two comlete genes for the 70 kdal heat-shock protein, and the aforementioned isolated sub-clone, plasmid 51 [Karch et al. (1981) J. Mol. Biol. 148: 219–230], contains a fragment of the first heat-shock gene in plasmid 132E3. This fragment was isolated by digestion of plasmid p51 with the restrition endonucleases BglII and BamHI.

Figure 1A:
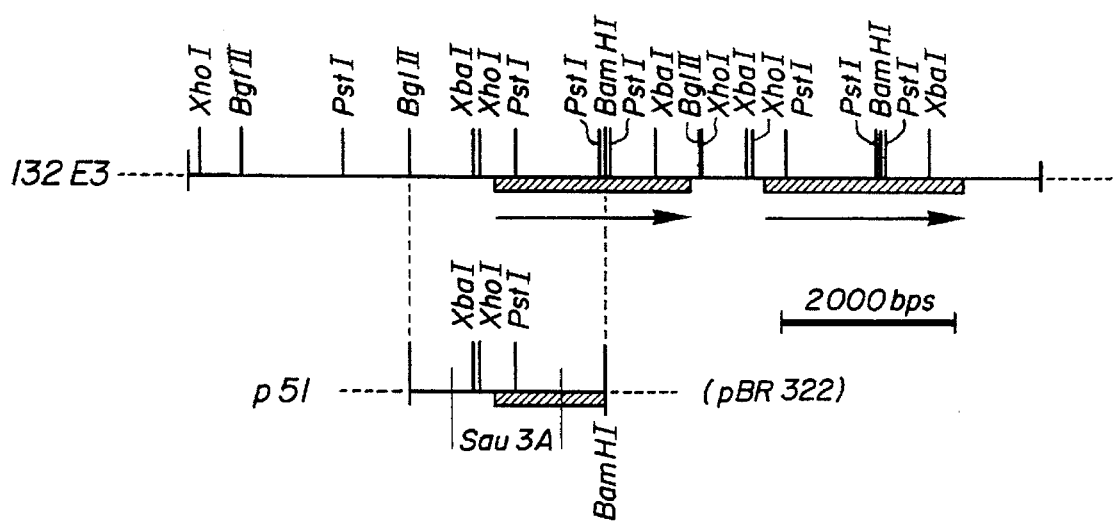
FIG. 1a is a schematic representation of a partial restriction map of part of plasmid 132E3 containing two 70 kdal heat-shock protein (hsp) genes (heavy lines) and their orientation (arrows). The lower part of FIG. 1a represents the relevant partial restriction map of plasmid 51 for comparison purposes.

The upper part of FIG. 1a is a representation of a portion of plasmid 132E3 indicating the two genes encoding 70 kdal heat-shock proteins (thick line segments) and some of the identified restriction sites. The lower part of FIG. 1a represents a portion of p51 containing the BglII-BamHI segment containing the aforesaid 650 bp fragment, bounded by the Sau3A cleavage sites.

Figure 1B:
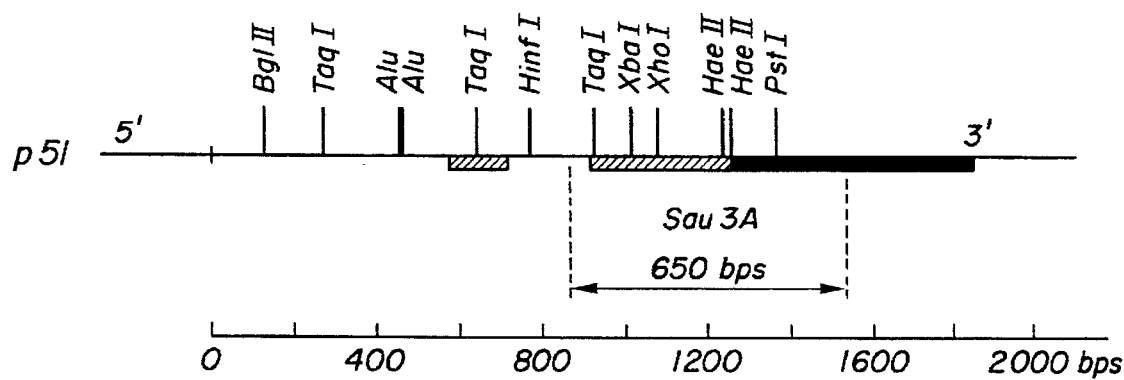
FIG. 1b represents on an enlarged scale a more detailed restriction map of part of plasmid 51 with additional restriction sites, including the two characteristic Sau3A sites.

FIG. 1b is a more detailed representation of the portion of interest contained in p51 with additional restriction sites indicated, and also showing the position of the 650 bp fragment between two Sau3A sites.

FIG. 2 provides the DNA sequence data for one strand contained in the aforementioned 650 base pair fragment. The limits of this sequence are indicated by the position of the Sau3A restriction sites (GATC). Also, XbaI, XhoI and PstI recognition sites for restriction are indicated, and the position of the transcription and translation start sequence are indicated by arrows 1a and 1b, respectively. The 650 bp fragment was functionally inserted into plasmid pMC1403 in a position to control the expression of test genes in this plasmid. Plasmid pMC1403 [Casadaban et.al. (1980) J. Bacteriol. 143: 971–980] is a derivative of plasmid pBR322 [Bolivar et.al. (1977) Gene 2: 95–113] containing the entire $E.$ $coli$ lac operon with the exception of the sequences coding for the first seven amino acids of β-galactosidase and all sequences 5' to the β-galactosidase protein coding region (promoter, ribosomal binding site, translation initiation codon). Consequently lac strains of $E.$ $coli$ such as MC 1061 [Casadaban et.al. (1980) J. Mol. Biol 138: 179–207] carrying plasmid pMC1403 do not produce β-galactosidase. A polylinker (EcoRI, SmaI, BamHI) at the 5' end of the lac sequences in pMC1403 permits the introduction of foreign DNA sequences upstream from the β-galactosidase coding region. Insertion of a segment containing a functional promoter and the RNA leader sequences will result in the production of β-galactosidase activity. It should be noted that the amino-terminal end of β-galactosidase is not essential for its enzymatic activity [Muller-Hill B. and Kania, J. (1974) Nature 249: 561–563]. All that is therefore required is that the inserted promoter/RNA leader sequence permits reading in the correct frame with the incomplete β-galactosidase coding region. Hence the 650 bp segment was ligated into the BamHI site of plasmid pMC1403, in front of the incomplete β-galactosidase gene. The new recombinant plasmid thus obtained (see FIG. 3) was designated pRV15. The procedure of this plasmid construction is shown in a diagrammatic form in FIG. 3. In this figure, the upper left part (FIG. 3a) represents a section of the aforementioned plasmid 51 containing the 650 bp fragment 2 to be cleaved out with Sau3A and to be inserted into the BamHI site of plasmid pMC1403 shown in FIG. 3b the truncated lac operon of the plasmid pMC1403 is represented by the heavy line with numeral 3 on the diagram of FIG. 3b. It also comprises a structural gene for ampicillin resistance. Plasmid p51 is digested with Sau3A to excise the aforesaid 650 bp fragment represented on the left of FIG. 3c by numeral 2; this fragment was purified from polyacrylamide gels (see FIG. 5c) by electroelution. This fragment was inserted into the BamHI site of pMC1403 in either orientation. The ligation mixture was then used to transform the lac strain of E. coli MC 1061. Transformants were plated on media containing ampicillin and Xgal (Xgal is 5-bromo-4-chloro-3-indolyl-N-D-galactoside) which is a substrate for β-galactosidase, and which after cleavage by the enzyme produces an identifiable colored product (see Miller, J. Experiments in Molecular Genetics, pp. 47–55, Cold Spring Harbor, N.Y. 1972). Plasmid pMC1403 did not produce β-galactosidase activity in this assay while plasmid pRV15 and a large number of other transformants, prepared in the aforesaid manner, were found to produce substantial amounts of β-galactosidase as determined by the color change produced on Xgal plates.

Figure 4A:
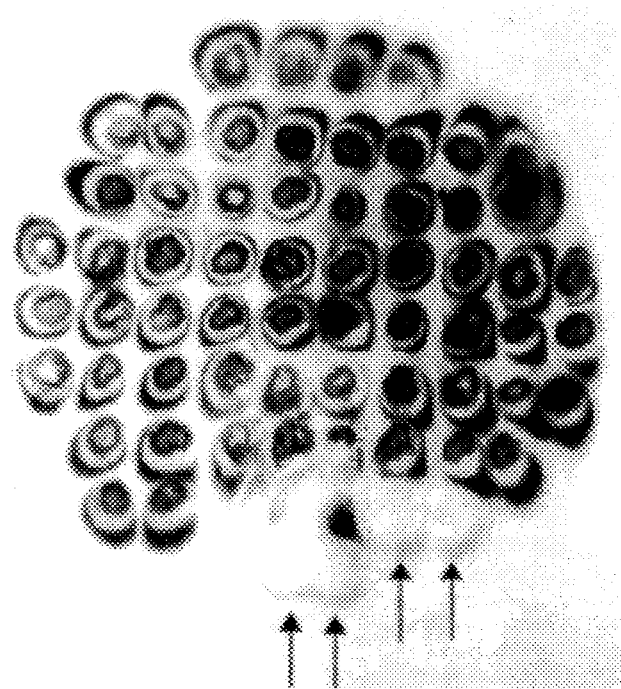
Figure 4B:
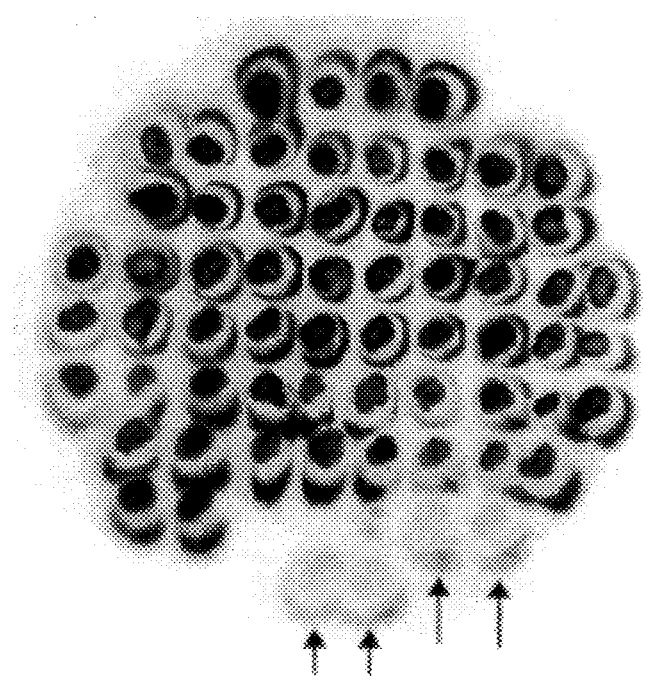
FIG. 4b represents a similar colony hybridzation assay but using the Sau3A 650 kbp fragment from plasmid 51 as a probe. Control colonies of pMC1403 are indicated by arrows.

In addition, β-galactosidase-coding plasmid constructions such as pRV15 were analyzed further by the colony hybridization assay of Grunstein [Grunstein and Hogness (1975) PNAS 72: 3961–3966] using either radioactively labelled 650 bp Sau3A fragments from p51 (see FIG. 4b) or the 2 kbp XbaI gene fragment (see FIGS. 1a, 4a) from plasmid 132E3 as hybridization probes. These fragments were radioactively labelled by the process of nick translation [Maniatis et.al. (1975) PNAS 72: 1184]. As seen in FIGS. 4a and 4b, all selected transformants hybridized to both radioactive probe DNAs demonstrating the presence of both DNA sequences in recombinant plasmids such as pRV15.

The presence of the 650 bp fragment containing the Drosophila 70 kdal heat-shock gene control element was confirmed by restriction analysis, see FIGS. 5a, b and c. Plasmid pMC1403 contains unique restriction sites for EcoRI and SalI, but no XhoI or XbaI sites. The Sau3A 650 bp fragment from plasmid p51 however contains unique sites for restriction by XhoI and XbaI but has no sites for restriction enzymes such as EcoRI and SalI. In contrast, recombinant plasmids such as pRV15 should contain unique sites for all four aforementioned enzymes (see FIG. 3). Restriction of recombinant DNA from plasmids such as pRV15 with XhoI and SalI or with XbaI and SalI should produce two fragments of about 4 and 6.5–7 kbp if the structure shown for pRV15 in FIG. 3 is correct. Plasmid pMC1403 however should only be linearized. FIG. 5a shows a photograph of DNA fragments produced by the aforementioned restriction enzymes after electrophoresis on agarose gels, and confirms the structure of plasmid pRV15 shown in FIG. 3. These results are presented again in FIG. 5b where it is also demonstrated that digestion with SalI, XhoI or XbaI individually only linearize pRV15, further confirming the structure shown in FIG. 3.

Further, if pRV15 contains the 650 bp Sau3A fragment of plasmid p51 inserted into the BamHI site of pMC1403, then it should be possible to recover the 650 bp Sau3A fragment by digestion of recombinant DNAs such as pRV15 with the restriction enzyme Sau3A. That this is the case is shown in FIG. 5c lane 7 by the arrows. In addition, the identity of the 650 bp excised fragment is confirmed by its restriction by XbaI or by XhoI. See FIG. 5c lanes 5 and 6.

The demonstration that the Sau3A 650 bp fragment and the β-galactosidase coding sequences are in the orientation shown for pRV15 in FIG. 3 is presented in FIGS. 6a and b. In FIG. 6a, the correct orientation is shown in a diagrammatic form from which the respective double digestions with EcoRI and XbaI or by EcoRI and XhoI would predict the excision of fragments from the 650 bp fragment, correctly oriented with respect to the β-galactosidase gene 12, of respectively 150 and 220 bp. In FIG. 6a, the arrow 11 indicates the transcriptional direction of the heat-shock control elements. The above prediction is demonstrated by the restriction gel analysis shown in FIG. 6b where EcoRI and XbaI double-digestion liberate an approximately 150 bp fragment, and EcoRI and XhoI double-digestion, a 220 bp fragment as evidenced by electrophoresis on 5% acrylamide gels. These experiments confirm that plasmid pRV15 has the desired orientation of control and coding elements shown in FIG. 3. The position of bands of sizes 515, 220 and 154 bp are indicated by arrows marked with the corresponding numbering.

The hybrid plasmid pRV15 and other identical isolates constructed as described in the preceding section, produce substantial amounts of β-galactosidase as determined by examining the color changes on Xgal plates. The presence of β-galactosidase protein produced in E. coli under the control of a Drosophila heat-shock control element has also been clearly demonstrated by immune precipitation of protein extracts of E. coli containing plasmid pRV15 after radioactive labelling a newly synthesized protein with $^{35}$S-methionine. A polypeptide of molecular weight approximately 120,000 daltons was precipitated from such protein extracts by immune sera directed against authentic E. coli β-galactosidase.

The details of the construction and expression of pRV15 are now set forth.

A. Construction of Plasmid pRV15

10 μg of plasmid p51 (FIG. 1a, lower part) were digested for 4 hours at 37° C. with 10 units of Sau3A (incubation buffers for this, and all other digestion described below as suggested by the supplier of the restriction enzymes: New England Biolabs Cat. 1982). The concentration of DNA during digestion with Sau3A was 40 μg/ml. The digestion products were electrophoresed on a non-denaturing 5% polyacrylamide gel in 1×TBE (10.9 g Tris base, 5.5 g boric acid, 0.93 g Na$_2$EDTA per liter H$_2$O) buffer. A Sau3A digest of pBR322 was electrophoresed in parallel and served to identify the 650 bp 51 Sau3A promoter fragment (FIG. 5c). DNA fragments were visualized with ethidium bromide (EtBr). The region containing the promoter fragment, indicated by the arrows in FIG. 5c, was cut out of the gel and the fragment was electroeluted into a dialysis bag. Electroelution was carried out for 5 hours at 200v in 1×TBE buffer. The eluate was collected in a 15 ml siliconized Corex tube and ethanol-precipatated overnight at −20° C. The precipitate was collected by centrifugation (Sorvall, 30 min., 10,000 rpm, SS34 rotor), dried in a lyophilizer and resuspended in 200 μl of TE buffer (10 mMTris. HCl, pH 7.5, 1 mM Na$_2$EDTA). The DNA was then extracted twice with TE-saturated phenol and twice with ether. The solution was then passed through a Sephadex G75 mini-column (in a Pasteur pipet). DNA in the column eluate was ethanol-precipitated twice, dried and resuspended in 20 μl of TE buffer. A 10 μl portion was incubated with several units of XbaI in the appropriate digestion buffer for 1 hour at 37° C. The partially digested DNA was electrophoresed on a 5% polyacrylamide gel. This experiment (FIG. 5c) demonstrated that the isolated segment was the 650 bp Sau3A fragment, since the promoter fragment includes the only XbaI site of plasmid p51.

One μg of plasmid pMC1403 was digested with 4 units of BamHI for 30 min. at 37° C. The digested DNA was extracted 3 times with phenol and then 3 times with ether. The DNA was further purified by 2 subsequent ethanol precipitations. The pelleted DNA was dried and then resuspended in 20 μl of TE buffer.

Ten μl aliquots of the solutions containing the 650 bp promoter fragment and digested pMC1403 were combined and then incubated overnight at 140° C. with an excess of T4 DNA ligase in a total volume of 25 μl (incubation buffer as recommended by New England Biolabs 1982 Cat.). The ligation mixture was then incubated for several hours with 8 units of BamHI at 14° C. Aliquots (1, 3 and 7 μl) were then used to transform 0.5 ml aliquots of $CaCl_2$-treated E. coli MC 1061. Aliquots (0.1 ml) of the transformation suspension were then placed on LB agar containing 10 μg/ml ampicillin and 40 μg/ml of Xgal. Blue colonies were observed after overnight incubation of the plates at 37° C. Approximately 80 β-galactosidase-producing colonies were isolated. The presence of the p51 Sau3A promoter fragment in the recombinants was established by Grunstein colony hybridization (FIG. 4b). The hybridization probes were prepared as follows: the p51 Sau3A promoter fragment was isolated as described above. 50 μg of 132E3 were digested with 50 units of XbaI for 2 hours at 37° C. The digestion products were separated on a 0.9% agarose gel. The 2 kbp 70 kdal heat-shock protein gene fragment was eluted electrophoretically from the gel and was purified as described above. The latter fragment and the p51 Sau3A fragment were then $^{32}$p-labelled by nick translation to a specific radioactivity of $2 \times 10^8$ cpm/μg. The two probes were then denatured and hybridized to two nitrocellulose filters containing DNA of the 80 selected transformants and of pMC1403 (FIGS. 4a, b). Both probes strongly hybridized to DNAs of all 80 recombinants, suggesting that all recombinants contained the 650 bp promoter fragment. Clones 5, 15, 25, 35, 45, and 55 were selected for further studies. Small quantities of DNA were prepared from each of these clones [Davis et.al. (1980) Methods in Enzymology, Grossmann and Moldave, eds. 65: 404–414]. These DNAs and pMC1403 DNA were compared further by restriction digestion and electrophoresis on 0.9% agarose gels (FIGS. 5a, b). The results indicate that restriction of the recombinant plasmids such as pRV15 with XhoI and SalI or with XbaI and SalI produce two fragments of 4 and 6.5–7 kbp, thus confirming the structure of plasmid pRV15 as shown in FIG. 3d.

B. Expression of the Drosophila Heat-Shock E. coli β-galactosidase Fusion Gene in E. coli Bacteria containing the hybrid plasmid pRV15 and other isolates constructed as described in the preceding section, produce substantial amounts of β-galactosidase as determined by examining the color changes in Xgal plates. The presence of a β-galactosidase protein produced in E. coli under the control of a Drosophila heat-shock control element was also demonstrated by immune precipitation [Bromley et.al. (1979) J. Virol. 31: 86–93] of protein extracts of E. coli containing plasmid pRV15 after radioactive labelling of newly synthesized proteins with $^{35}$S-methionine. A polypeptide of molecular weight about 120,000 daltons was clearly precipitated from such protein extracts by immune sera directed against authentic E. coli β-galactosidase.

C. Expression of Heat-Shock β-galactosidase Hybrid Gene in Xenopus Oocytes

Plasmid pRV15 (50–100 ug) was digested with an excess of SalI and EcoRI. The two resulting restriction fragments were then separated on 0.85% agarose gels. The 7 kb fragment containing the hybrid gene but no vector sequences was purified by electroelution and gel filtration on Sephadex® G75. This fragment was then incubated with an excess of T4 DNA ligase in a total volume of 25 μl as described above, to permit circle formation. The ligated fragments were injected into oocytes as described in Voellmy and Rungger (1982) PNAS 79: 1776–1780. Following a 6–20 hours preincubation at 20° C., the oocytes were injected a second time with ∝–$^{32}$P-GTP and either heat-treated for 2 hours at 37° C. or kept at 20° C. for the same period. Total RNA prepared from these oocytes or from oocytes that did not contain foreign DNA was hybridized to Southern blots of Sal I/Eco RI digests of plasmid pMC1403. Oocytes that did not contain the hybrid gene did not produce measurable amounts of RNA complementary to the β-galactosidase gene. Both heat-treated and untreated oocytes containing the pRV15 fragment were found to have made β-galactosidase RNA in approximately similar quantities.

In another series of experiments, unlabelled RNA was isolated from oocytes containing the hybrid gene which had been either heat-treated for 2 hours or incubated at 20° C. for the same time in the presence or absence of low concentration of ∝-Amanitin [Voellmy and Rungger (1982) PNAS 79: 1776–1780]. The oocyte RNAs were labelled by reverse transcription as described by Bromley et.al. (1979) J. Virol. 31: 86–93, and hybridized to pMC1403 Southern blots. Again β-galactosidase transcripts were present in RNAs for heat-treated and untreated oocytes. ∝-Amanitin did stop transcription of the hybrid gene at both temperatures indicating that RNA polymerase B (i.e. II) was responsible for all observed transcriptional activity.

2. The Construction and use in Eukaryotic Cells of Plasmid PR84 which Contains a Human Influenza Virus Haemagglutinin Gene under the Control of a Drosophila Heat-shock Control Element A plasmid denoted 520 was constructed from plasmid pRV15 and plasmid pSVod [Mellon et.al. (1981) Cell 27: 279–288] which is capable of replicating either in procaryotic cells or in certain eukaryotic cells. Plasmid 520 allows rapid analysis of transcriptional control since it includes the SV40 virus origin of replication and is able to replicate efficiently in SV40 mutant-transformed, transformation antigen positive COS cells [Gluzman (1981) Cell 23: 175–182].

The schematic form of the construction of plasmid 520 is shown in FIG. 2, Plasmid pRV15 (FIG. 7a, representation in linear form) was digested with SmaI, subsequently digested with SalI and the resulting 7 kbp fragment (FIG. 7c) containing the 650 bp Drosophila control element 2 and the lac gene fragment 3 originating from pMC1403 present in pRV15 was isolated by electrophoretic elution from a preparative agarose gel.

Plasmid pSVod (FIG. 7c) was digested with BamHI, the cohesive ends were filled in with DNA polymerase Klenow fragment and the DNA finally digested with SalI. In FIG. 7c, numeral 10 indicates the site of the deletion of the 1 kb pBR322 sequence which has been claimed to be inhibitory for replication in eukaryotic cells. The truncated pSVod fragment (FIG. 7d) so formed was ligated to the 7 kbp fragment isolated from pRV15, and the ligation mixture was used to transform E. coli MC1061. The structure of plasmid 520 is shown in FIG. 7e in which a more detailed representation of the 650 bp segment also appears with the XbaI, XhoI and PstI restriction sites. Another restriction site (PvuII) is also indicated and corresponds to the CAGCTG sequence between 60 and 70 bp, as denoted in FIG. 2. The significance of the PvuII site will be mentioned hereinafter. Plasmid 520 is shown in circularized form in FIG. 8a where the segments a, y and z represent genes of the lac operon. Numeral 11 designates the fragment containing the SV40 origin.

Transformants were plated out on Xgal-Ampicillin plates as described previously, and blue transformants suspected of containing plasmid 520 were isolated. From the structure shown in FIG. 8a, plasmid 520 should provide the following size fragments when digested with the named restriction enzyme combinations.

| Fragment sized in kbp | Enzymes |
| --- | --- |
| 0.75/1.1/8.5 | PstI/EcoRI |
| 2.6/7.2 | HindIII/SalI |
| 3.1/6.7 | SalI/XbaI |

The 520 plasmids indeed produced fragments of the correct sizes when digested as evidenced in the gel analyses of FIGS. 8b, c and d. Other fragments produced by various combinations of enzyme digestions serve as controls for the interpretion of the digestions noted above.

Plasmid p81 places a gene which encodes for a eukaryotic protein in the correct reading frame with the 650 bp heat-shock control element of p520. As starting material for this construction, plasmid A/PR 8/ms/34 (Mount Sinai) Clone No. 4.76 containing a human influenza haemagglutinin gene (1775 bp, numeral 20) inserted into the PvuII site of vector PAT 153/Pvu II/8 was obtained from Dr. G. Brownlee (University of Oxford, Department of Pathology, U.K.). The plasmid containing the haemagglutinin (HA) gene (insert 20, see FIG. 9) was digested with BamHI, and the ends were filled in with DNA polymerase Klenow fragment. Following digestion with HindIII, the haemagglutinin gene fragment was purified on agarose gels. The insert 20 contains a complete HA protein coding sequence, an RNA leader segment, and 40 bp of 3' nontranslated sequence. The HA gene-containing fragment was inserted into plasmid vector pSVod to produce plasmid PR81 as follows: pSVod DNA was digested with SalI, ends were filled in as described above, and the DNA was further digested with HindIII (see structure in FIG. 9b). The HA fragment 20 and the SalI/HindIII digest of pSVod were ligated together using T4 DNA ligase in the presence of BamHI and SalI to give PR81 (see FIG. 9c), and the ligation mixture was used to transform E. coli C 600.

Transformants were analyzed for the presence of PR81-like plasmids (for predicted structure, see FIG. 9c) as follows: Grunstein colony hybridization was performed in a manner similar to that described earlier in connection with pRV15 (see FIG. 4). A nick translated probe of the HA gene (BamHI/HindIII fragment from pA/PR 8/34/ms/4.76 kb) was prepared and hybridized to the PR81-like transformants (see FIGS. 9d and 9e). FIGS. 9d and 9e show the autoradiograms of eight colonies. It can be seen from FIGS. 9d and 9e that this DNA probe hybridizes to most of the transformants. Negative controls are provided by the pSVod containing colonies indicated in the figure by arrows.

PR81-like plasmids were further characterized by restriction analysis, as shown in FIG. 9f. The structure indicated for PR81 in FIG. 9c is verified by the formation of DNA fragments of the following sizes after digestion with the restriction enzymes indicated below:

| Plasmids | Sizes of Fragments kbp | Enzymes used |
| --- | --- | --- |
| PR81 | 3.2, 1.5–1.6 | EcoRI |
| PR 8/34 | 3.8, 1.3 | EcoRI |
| pSVod | 3.3 | EcoRI |
| PR81 | 4.5 | HindIII/SalI |
| PR 8/34 | 3.3, 1.7–1.8 | HindIII/SalI |
| pSVod | 2.7, 0.6–0.7 | HindIII/SalI |

The results provided in FIG. 9f indicate the presence of the above fragments.

The construction scheme for plasmid PR84 is presented in FIGS. 10a to 10e. Briefly, plasmid PR84 places the Ha gene under the control of expression control region of the Drosophila heat-shock gene described heretofore. The hybrid gene itself is placed under the replication control of plasmid pSVod. Digestion of plasmid 520 (FIG. 10a) with PvuII and NcoI results in the formation of two fragments of about 1 kbp in length, one of which (FIG. 10b) contains part of the SV40 origin of replication sequence and part of the 650 bp heat-shock control element, including 400 bp of 5'-nontranscribed sequence and 60 bp of the RNA leader sequence. The two 1 kbp fragments were isolated by electrophoresis on preparative gels of 1.2% low melting agarose.

Plasmid PR81 (FIG. 10c) was digested with HindIII, the ends were filled up with DNA polymerase Klenow fragment, and the DNA was further digested with NcoI which has a unique cutting site in this plasmid situated within the SV40 origin of replication sequence (see FIG. 10d). The resulting PR81 fragments were ligated with the 1 kbp fragments isolated from plasmid 520 and the ligation mixture was used to transform E. coli C 600. The resulting transformants include plasmids such as PR84 whose predicted structure is shown in FIG. 10e.

A more detailed structure for PR84 including partial DNA sequence predictions are presented in FIG. 10f in the form of a single strand representation of plasmid sequences. As shown in FIG. 10f, PR84 comprises from the 5' end, successively, a 250 bp origin of replication segment of SV40 origin, a 346 bp sequence from pBR322, a 400 bp Drosophila 5' nontranscribed sequence [p51; p132E3, see Karch et.al. (1981) J. Mol. Biol. 168: 219–230] originally included in the 650 bp heat-shock control sequence, a Drosophila 65 bp hsp gene RNA leader fragment (base pairs numbered 1 to 65), a linker segment of 8 base pairs, a haemagglutinin (HA) RNA leader segment (base pairs numbered 1–32), a HA signal peptide coding segment (base pairs numbered 33–83) and a HA protein coding segment (bp 84 onwards).

The rather complicated construction scheme chosen for plasmid PR84 checked by restriction digest analysis of the parent plasmids used, the results of which are shown in FIG. 11a. The following restriction sites are predicted for the plasmids:

PR81: 1NcoI site, 1 HindIII site, the NcoI site in the SV 40 origin of replication sequence.

PR 8/ms/34:1 NcoI site, no site in HA gene.

520: 1 NcoI site, several PvuII sites in the lac operon a pair of 1 kbp NcoI/PvuII fragments, one of them containing the origin-hsp 70 promoter fragment.

That these predictions fit with the structures of these plasmids illustrated in the construction schemes is shown by the results of the restriction analyses indicated by the gel patterns in FIG. 11a. The two 1 kbp NcoI/PvuII fragments are clearly seen and are indicated in FIG. 11 (lane 17) by an arrow.

Further characterization of PR84-like plasmids was performed using the Grunstein colony hybridization procedure described before (see FIG. 4). In this case, a nick translated probe (approximately $10^8$ cpm/μg) of the Sau3A/XhoI fragment from plasmid p51 (containing the Drosophila hsp control element) was employed, and the results are presented in FIG. 11b).

A number of the positive colonies identified in this way were grown up for the preparation of small amounts of each plasmid as described previously, and a series of restriction analyses were performed. The gel patterns so obtained are shown in FIGS. 11c and d. The expected pattern of digestion products formed by XhoI digestion as predicted from the structure of PR84 presented in FIG. 10 are: one XhoI fragment of 405 bps and one very large fragment. FIG. 11c shows the results of this analysis and the plasmid clones in lanes 2, 4, 6 and 8 have the expected pattern as compared to the HinfI standard digest pattern of pSVod. These plasmids were selected for further analysis where they were digested either with XhoI/NcoI or with XbaI/NcoI. The results obtained are shown in FIG. 11d. The expected sizes of fragments produced from the map shown in FIG. 10 would be one fragment of about 700 bp and one of 405 bp with XhoI/NcoI and one large fragment, and with XbaI/NcoI, one fragment of 650 bp and one large fragment. FIG. 11d shows the validity of these predictions for all of the plasmids analyzed.

DNA from plasmid PR84 was used to transfect eukaryotic cells. As suitable cells for bringing about such experiments COS cells [Gluzman (1981) Cell 23: 175–182] were selected because of their usefulness for the rapid expression analysis of gene constructions [Gething and Sambrook (1981) Nature 293: 620–625]. After transfection, the cells were incubated at either 37° C. or 42° C. in the presence of labelled methionine ($^{35}$S). Then the contents of the cells were analyzed by immune precipitation using rabbit antiserum raised against PR 8/ms influenza virus (a gift of Dr. J. Skehel, M.R.C. Laboratories, Mill Hill, London U.K.). The complexes purified on Protein A-Sepharose® were finally subjected to electrophoresis on polyacrylamide gels and identified by fluorography. The analytical results indicated the presence in good yield of a protein ($M_r$=75,000) indistinguishable from authentic glycosylated haemagglutinin [Elder et.al. (1979) Virology 95: 343–350]. Synthesis of haemagglutinin occurred both at 37° C. and to a lesser extent at 42° C. No such specific polypeptides were observed using any other transfecting DNA than of PR84 nor in immune complexes other than with anti-PR 8 antisera.

The details of the construction and expression of the eukaryotic expression vectors are now set forth.

A. Construction of Plasmid 520

Fifty μg of plasmid pRV15 were digested first with 50 units of SmaI for 2 hours at 37° C. and subsequently with 50 units of SalI for 2 hours at 37° C. (buffers as recommended by New England Biolabs). The digest was then electrophoresed on a 0.9% agarose gel. The region containing the 7 kb lac fragment was cut out of the gel, and the DNA was recovered by electroelution (200 v. 6 hours).

DNA in the eluate was collected by ethanol precipitation. The fragment was then dried and resuspended in 200 μl of TE buffer, phenol- and ether-extracted twice, and then passed through a small Sephadex® G75 column as described before. The DNA in the column eluate was collected by ethanol precipitation.

Ten μg of plasmid pSVod were digested with 10 units of BamHI for 2 hours at 37° C. The digested DNA was purified by 3 phenol-extractions, 3 ether-extractions and 2 ethanol precipitations. The dried DNA was then resuspended in TE buffer and incubated with several units of DNA polymerase Klenow fragment in the presence of 0.5 mM deoxyadenosine triphosphate (dATP), deoxycytidine triphosphate (dCTP), deoxyguanosine triphosphate (dGTP) and deoxythymidine triphosphate (dTTP) at 6°–7° C. for one hour. The DNA was purified again by repeated phenol- and ether-extraction and ethanol precipitation. The purified DNA was then digested with 10 units of SalI for 2 hours at 37° C. The digestion products were purified again as described above. The 7 kbp pRV15 SmaI/SalI fragment and the above described pSVod fragments were then incubated overnight (in a molar ratio of 10:1) with an excess of T4 DNA ligase at 14° C. This ligation mixture was used to transform E.coli MC 1061. SmaI and BamHI were included in the ligation mixture. Transformants were plated on LB plates containing 10 μg/ml ampicillin and 40 μg/ml Xgal. Blue transformants were isolated. DNA from such recombinants was prepared as described by Schedl et.al. (1978) Cell 14: 921–929. Recombinants were identified by restriction analyses.

B. Construction of Plasmid PR81

Fifty μg of plasmid A/PR 8/34 Clone No. 4.76 obtained from Prof. G. Brownlee, University of Oxford, U.K. were digested with 30 units of HindIII and BamHI for 2 hours at 37° C. The digest was electrophoresed on a 0.85% agarose gel. The HindIII-BamHI haemagglutinin gene fragment was purified by electroelution as described above. Aliquots of this DNA were nick translated to serve as probes for identifying PR81 and similar recombinants by Grunstein colony hybridization (specific radioactivity of probes about $10^8$ cpm/μg).

Fifty μg of A/PR 8/34/4.76 were digested with 50 units of BamHI for 2 hours at 37° C. The DNA was phenol-extracted three times, ether-extracted and ethanol-precipitated. The dried DNA was then resuspended in 25 μl of TE buffer and incubated with several units of DNA polymerase Klenow fragment and 0.3 mM of all four deoxynucleotide triphosphates in a total volume of 100 μl for 90 minutes at 6°–7° C. The DNA was then purified by phenol- and ether-extractions as above. Following ethanol precipitation, the DNA was dried and then resuspended in 25 μl of TE buffer. It was digested subsequently with 54 units of HindIII for one hour at 37° C. The digested DNA was repurified by phenol-extraction.

Ten μg of plasmid pSVod [Mellon et.al. (1981) Cell 27: 279–288] were digested with 30 units of SalI for one hour at 37° C. The DNA was purified by phenol-extraction as above and was then incubated with several units of Klenow fragment in 100 μl in the presence of 0.5 mM, dATP, dCTP, dGTP and dTTP for one hour at 37° C. Following repurification by phenol-extraction, the DNA was digested further with 25 units of HindIII for one hour at 37° C. and repurified by phenol extraction.

An A/PR 8/34 digest (1.5 μg) and a pSVod digest (2 μg) were incubated overnight at 14° C. with an excess of T4 DNA ligase in a total volume of 30 μl. Several units of BamHI and SalI were included in the ligation mixture. The ligated DNA was purified by phenol extraction as described above. It was then digested with 6 units of BamHI for one hour at 37° C., followed by incubation with 12 units of SalI for one hour at 37° C. Aliquots of this reaction mixture were used to transform $CaCl_2$-treated E.coli C 600. Transformants were isolated on LB plates containing 10 μg/ml ampicillin. About 350 clones were purified and analyzed by colony hybridization using the nick translated BindIII-BamHI haemagglutinin gene fragment described above as probe. Approximately 80–90% of the clones were found to contain a haemagglutinin gene insert.

Seven of the positive clones were grown up, and DNA was prepared from them. These DNAs were compared with the original clones A/PR 8/34 and pSVod by restriction digestion and electrophoresis on a 0.9% agarose gel.

| Predicted Fragment Sizes | |
| --- | --- |
| Digestion with EcoRI | |
| Recombinants | 3.2 kbp, 1.5–1.6 kbp |
| A/PR 8/34 | 3.8 kbp, 1.3 kbp |
| pSVod | 3.3 kbp |
| Digestion with HindIII and SalI | |
| Recombinants | 4.5 kbp |
| A/PR 8/34 | 3.3 kbp, 1.7–1.8 kbp |
| pSVod | 2.7 kbp, 0.6–0.7 kbp |

Five out of the seven recombinants that were analyzed showed the expected digestion pattern. PR81 is one of these five clones.

PR81 DNA was prepared as described by the method of Schedl et.al. (1978) Cell 14:921–929 and was analyzed further by restriction enzyme digestion.

C. Construction of Plasmid PR84 p520 DNA (75 µg) was digested with 25 units of PvuII for one hour at 37° C. and subsequently with 20 units of NcoI for 2 hours at 37° C. The digest was electrophoresed on a 1.2% low melting agarose gel containing 0.05 µg/ml EtBr. The region including the two 1 kbp NcoI/PvuII fragments (one of them is a hsp 70 gene promoter fragment) was cut out of the gel. The agarose piece and 10 volumes of TE buffer were heated to 65° C. for 10 minutes, and the DNA was extracted subsequently with an equal volume of phenol. After one additional phenol/chloroform and 3 ether extractions, the DNA was precipitated two times with ethanol.

PR81 DNA (10 µg) was digested with 15 units of HindIII for one hour at 37° C. Following purification by phenol extraction the DNA was incubated with several units of Klenow fragment and 0.5 mM of all four deoxyribonucleotide triphosphates for one hour at 6°–7° C. After repurification, the DNA was digested with 10 units of NcoI for 90 minutes at 37° C. and was repurified by phenol extraction.

Aliquots (0.25 µg) of the p520 1 kbp NcoI/PvuII fragments and aliquots (0.05–0.1 µg) of the PR81 fragments were incubated overnight at 14° C. with an excess of T4 DNA ligase. This mixture was used to transform E. coli C 600. About 600 ampicillin-resistant transformants were isolated and examined by Grunstein colony hybridization using a nick translated p51 Sau3A/XhoI promoter fragment as a probe (approximately $10^8$ cpm/µg) (FIG. 11b).

Ten positives were grown up and DNA was prepared from these clones. Aliquots of their DNAs were digested with XhoI and were analyzed on 5% polyacrylamide gels.

The presence and sizes of XhoI fragments provided good evidence for the presence in the recombinant DNAs of both the hsp 70 kdal gene promoter and the haemagglutinin gene. Four out of the 10 clones tested showed the expected restriction pattern (two fragments: one large, about 5 kbp, and one of 400 bp) (FIGS. 11c and d).

Additional digestions with NcoI/XhoI and XbaI/NcoI confirmed our initial analysis. PR84 is one of the four plasmids which have the correct structure.

D. Expression Experiments, Using Plasmid PR84

COS-I cells [Gluzman (1981) Cell 23: 175–182] were maintained in Dulbecco's MEM with 10% new-born calf serum and were subcultured one day prior to transfection to give cultures containing about $10^6$ cells per 6 cm diameter petri dish after further one day of culture. Transfection of cells was performed as follows:

The medium was removed from cell cultures at room temperature and the cultures were washed twice with 5 ml of phosphate-buffered saline (PBS). Subsequently one ml of the following preparations per dish were added.

1. 1 ml of Dulbecco's MEM with no serum, but containing DEAE Dextran (500 µg) and chloroquine (200 µg).

2. As 1, but containing in addition, 10 µg of plasmid 520 DNA.

3. As 1, but containing in addition, 10 µg of plasmid PR84 DNA.

Transfections were performed on 5 dishes of cells for each of the three conditions stated above.

Cell cultures were maintained at room temperature for 30 minutes with occasional gentle rocking to distribute the transfection solution over the entire cell culture. After removal of the transfection solution, 5 ml per dish of Dulbecco's MEM with 10% serum was added. Cell cultures were further incubated at 37° C. for 36 hours. Half of the two cultures were incubated at 42° C. for the last 4 hours of this period. After this period, the medium was removed and cultures were washed once with a Dulbecco's MEM containing 3 mg/l of L-methionine and 1% newborn calf serum. Cell cultures were labelled by addition of 1 ml of this same low methionine medium per dish but in the presence of $^{35}$S-Methionine (50 µCi/ml, 968 Ci/mmol). Cultures were incubated for one hour at either 37° C. or 42° C. in the case of the heat-shock samples. After this period of labelling, the 35S-Methionine medium was removed, the cultures washed three times with ice-cold PBS, and cells were scraped off in 1 ml of NET buffer (0.1M NaCl, 0.01M Tris-HCl pH 7.8, 0.001M EDTA, 0.5% NP 40). After vigorous pipetting to break down the outer cell membranes, nuclei and cellular debris were removed by centrifugation at 5000×g for 5 minutes at 4° C. The cytoplasmic supernatants were removed and aliquots were taken for immune precipitation as follows:

Aliquots (500 µl) of cytoplasmic extracts were kept on ice, 5 µl of specific antibodies were added and the solutions were mixed gently at 4° C. for two hours. The antibodies used were the following: Normal rabbit antiserum, antiserum raised against purified E.coli β-galactosidase, and antiserum raised against PR8 influenza virus obtained from Dr. J. Shekel, MRC Laboratories, Mill Hill, London, U.K. Anti HA antisera was preadsorbed for 30 minutes in NET buffer using cytoplasmic extracts of unlabelled COS cells prior to use for immune precipitation of labelled samples.

Antigen-antibody complexes were isolated by the addition of 50 µl of a 50% suspension of protein A-Sepharose® (Pharmacia), continuing the shaking at 4° C. for one hour, and recovering the bound complexes by centrifugation at 15,000×g for one minute. The complexes on protein A-Sepharose® were washed and centrifuged four times using 1 ml of NET and three times using 1 ml of RIPA buffer (0.15M NaCl, 0.05M Tris-HCl pH 7.5, 0.02M EDTA, 1M Urea, 1% Triton×100, 1% sodiumdeoxycholate). The final Sepharose pellets were boiled for 3 minutes in 100 μl of sample buffer [Laemmli (1970) Nature 227: 680–685]. After centrifugation at 15,000×g for 1 minute, the samples were subjected to electrophoresis on 10% polyacrylamide gels as indicated by Laemmli (1970) supra.

In the case of cell cultures transfected with plasmid PR84 DNA and in which the labelled cytoplasmic extracts were immune precipitated with antiserum raised against PR8 influenza virus, the gel analysis by fluorography [Laskey and Mills (1975) Eur. J. Biochem. 56: 335–341] clearly indicated the presence of a protein which is indistinguishable in size ($M_r$=75,000) from authentic glycosylated haemagglutinin [Elder et.al. (1979) Virology 95: 343–350]. Some possible processing to give polypeptides of $M_r$ approximately 42,000 and 36,000 was observed in some of these experiments. Synthesis of haemagglutinin occurred both when labelling was performed at 37° C. and to a lesser extent at 42° C. No such specific polypeptides were observed using any other transfecting DNA than PR84, nor in immune precipitations other than with anti PR8 antisera.

In a second series of similar transfection experiments, COS cells transfected with PR 84 were subjected to a period of heat-shock of five hours at 42° C. and were subsequently labelled with $^{35}$S-Methionine as described above but at 37° C. for 14 hours. Subsequent immunoprecipitations with anti HA antisera indicated a larger quantity of HA product than in non heat-treated samples labelled under similar conditions.

These results suggest that the Drosophila heat-shock promotor functions better at the heat-shock temperature in monkey cells than at the 37° C. control temperature. Some activity of this promotor at 37° C. is perhaps to be expected as we have previously noted the use of 37° C. as the heat-shock temperature for Drosophila cells. The improved synthesis of HA when cells are returned to 37° C. after a period of heat-shock suggests that the translational control of the Drosophila heat-shock promotor fragment, in particular the Drosophila ribosome binding site is non-functional or poorly functional in monkey cells at least at the higher temperature. Thus it is possible that although promotion of transcription occurs at 42° C. using the Drosophila DNA sequences, ribosome binding and initiation of translation may occur using the HA ribosome binding site, optimally at 37° C.

According to the present invention, expression vectors are provided which yield efficient transformation of eukaryetic hosts and high levels of expression within the host. In particular, the transcriptional/translational control region of a 70 kdal heat-shock protein has been isolated and joined to a replication system derived from a simian virus. A human influenza virus haemagglutinin gene was inserted into the resulting vector under the control of the said control region, and the resulting plasmid used to transfect a mammalian cell culture and apparently glycosylated haemagglutinin was produced.

Construction of Plasmid p629

A further Drosophila control element/HA gene construction was made to extend the utility of plasmid constructions such as PR84. The Ha gene being a vital gene is rather specialized as a model for any eucaryotic gene with its 3' end signals, and its RNA leader sequence, hence the PR84 construction contains both an HA RNA leader and a Drosophila RNA leader.

As a more general example of the construction of a gene expression unit using heat-shock control elements plasmid p629 was constructed. This plasmid contained in addition to the Drosophila heat-shock promoter the entire heat-shock RNA leader region, but was attached to a HA gene lacking the first 40 amino acid codons. For convenience, a plasmid p622b (a gift and personal communication of R. Voellmy) was employed; this plasmid contains a 450 bp XhoI/BglII fragment carrying the Drosophila hsp 70 promotor and RNA leader sequence (represented by the XhoI/Sau3A fragment of plasmid pRV15 described earlier). p622b is a derivative of the COS cell vector pSVod. The sequence around the BglII site is given below:

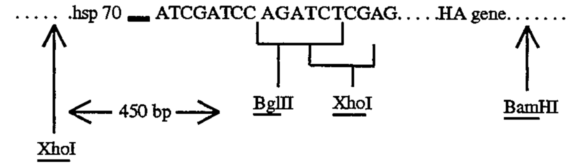

Experimental Construction of p629

15 μg of p622b were digested with 12 units (per 15 min) of BglII, and 15 μg of PR 8/ms/34 with 15 units of XhoI. Digests were for 2 hours at 37° C. The DNAs were then extracted three times with phenol, three times with ether and precipitated two times with ETON. Both DNAs were resuspended in 20 μl of TE buffer and ends were filled in a reaction involving several units of DNA polymerase (Klenow fragment) and 0.5 mM of each of the four dNTPS (total volume: 100 μl; reaction at 6° C. for 2 hours). Both DNAs were again phenol-extracted and purified as above and again dissolved in 20 μl of TE buffer. They were then digested individually with 15 units of BamHI (total volume 100 ul; 37° C. for 2 hours). Following phenol extraction the DNAs were collected by EtOH precipitation and dissolved in 15 μl of TE buffer. Different sets of ligations containing 1 μl of 622b digest and 1–5 μl of PR 8/ms/34 digest in a total volume of 25 μl were carried out (enzyme: 1–2 μl, T4 DNA ligase, New England Biolabs) incubated overnight at 14°. The ligase was inactivated at 65° C. for 10 min and the samples were then digested with several units of ClaI and SalI (successively, using the conditions suggested by New England Biolabs) for 2 hrs at 37° C. in volumes of 50 μl. The DNA mixtures were then used to transform *E. coli* MC1061.

About 300 individual transformants were characterized further using the Grunstein colony hybridization assay. Two separate sets of hybridizations were carried out: probes used were: a) the 450 bp Xhg-BglII fragment from p622b and b) the 1775 bp HindIII/BamHI gene fragment from PR8.4.76. Fragments had been separated in low melting agarose gels and were subsequently eluted from these gels. They were then labelled by nick translation ($10^7$–$10^8$ cpm/ug; $10^6$ cpm/filter). Eight (8) colonies that hybridized to both probes were selected, (see FIGS. 12*c* and *d*) and DNA was prepared from them using the mini-DNA preparation procedure described previously. The DNAs were digested with XhoI or with BglII/EcoRI and the digests were analyzed on 5% polyacrylamide gels. XhoI was expected to yield two fragments with sizes of 450bp and of about 5 kb. The BglII/RI digest should give fragments of 1130 bps, 1100 bps and of about 2.6 kb. Three of the eight clones tested had the correct restriction patterns (see FIGS. 12*a* and *b*).

Expression experiments using plasmid p629

Transfection of COS I cells was performed in a manner analogous to that described for the expression experiments using plasmid PR84. Immune precipitations performed as described previously, precipitated one major and a number of minor polypeptides of M.Wt around 75,000 daltons. When $^{35}$S-Methionine labelling was performed in the presence of 1 ug/ml tunicamycin, one major band ($M_r$=75,000) alone was observed, suggesting that the minor bands were the result of glycosylation. Synthesis of HA protein was greater during a labelling period of 14 hrs at 37° C. following a period of heat-shock than in parallel labeling periods in the absence of heat-shock.

3. HEAT SHOCK PROMOTERS USED FOR THE INDUCIBLE EXPRESSION OF GENES ENCODING SECRETABLE AND NON-SECRETABLE PROTEINS

Promoters of 70 kd heat-shock protein (hsp70) genes of human and Drosophila origin have been used to express a number of different genes in a heat-inducable fashion. We have chosen a chicken lysozyme and a human growth hormone gene as examples of genes that encode secretable proteins; in addition, the non-secretable genes encoding *E. coli* β-galactosidase and a human influenza virus haemagglutinin have been expressed in an analogous fashion. Hybrid genes have been introduced into widely divergent cell types, in which they have been observed to direct the synthesis of encoded proteins in a fully heat-inducible manner. An important fraction of the recombinant chicken lysozyme and of the human growth hormone produced by different cell types was found in the culture medium. This indicates that the posttranslational modifications that are necessary for the secretion of these proteins could be carried out properly by the different cells in which the heterologous hybrid gene constructs were used. In addition, the heat-induced, hybrid gene-directed synthesis of *E. coli*-specific β-galactosidase has been shown to provide a direct and convenient measure of efficiencies of functional DNA transfection in a wide variety of cell types.

There have been numerous attempts in recent years to use both procaryotic and eucaryotic expression systems to produce proteins of medical interest. Recently, eucaryotic expression of human genes has become of particularly great interest as a result of a better understanding of the physiological importance of precise posttranslational modifications (13). Where the gene product of interest, when produced in high concentration, proves toxic or otherwise inhibitory to large scale cell cultivation (19), there is an additional requirement for the synthesis of this protein under the control of an inducible promoter.

Amongst the inducible eucaryotic promoter systems that have been considered, the more prominent ones are those derived from various metallothionein genes and those from certain retroviruses, in particular mouse mammary tumor virus (MMTV). The metallothionein gene promoters of both mouse and human origin have been described (17,18), but both the degree of inducibility at the protein level (1.3 to 2.5 fold using a Bovine Papilloma virus vector, ref. 33) as well as the practicality of induction in large cell cultures remain problematic. The MMTV promoter, inducible by glucocorticoid hormones (5), has been used to express, for example, the thymidine kinase gene in mouse cells (15), but this system shares the inconvenience of hormone induction in mass culture and adds the unknown risk of using a tumor virus sequence; in addition a limited host range of applications is available for this system.

There exists a group of ubiquitous protein genes that is inducible by stress, for instance in the form of slightly elevated temperature (37). Several of these heat shock genes have been shown to be transcribed correctly and in a heat-regulated fashion in a variety of different eucaryotic cell types (1,3,4,7,8,9,23,25,32,34,35,41,42). The considerable strength of heat-shock gene promoters, (the seven *D.melanogaster* heat-shock proteins accumulate to a level of about 10% of the total protein within a few hours of heat treatment: ref.2) combined with the observation that they are active and inducible in a variety of cell types, suggests that they could serve as extremely valuable tools for the production of even complex eucaryotic proteins. It seems likely that many important posttranslational modifications are either cell type-specific or occur only in a selected number of cell types (10,36). The versatility of the heat shock promoter system may permit the expression of a given gene construct in a large number of different cells and may, therefore, obviate a search for a homologous promoter system for every specific expression problems.

Limited information was available concerning the capability of the control elements of heat-shock genes to direct the synthesis of foreign proteins. While the expression of the bacterial proteins β-galactosidase (1,4,9,23,25) and chloramphenicol acetyltransferase (8) under the control of eucaryotic heat shock promoters has been reported previously, there is, to our knowledge, little data that demonstrates the synthesis, driven by a heat-inducible promoter, of eucaryotic proteins. An exception is a recent study which showed the heat-inducible expression of a Drosophila alcohol dehydrogenase gene in transformed Drosophila flies (3,20). Herein, we describe the heat-inducible synthesis of *E. coli* β-galactosidase, human influenza virus haemagglutinin, chicken lysozyme and human growth hormone in a variety of cell types. Observation of the inducible synthesis of chicken lysozyme and human growth hormone in a secretable form demonstrates the potential of the heat-shock expression system for the production of proteins of medical interest, many of which function only after secretion.

MATERIALS AND METHODS

Hybrid Gene Constructions

The construction of the *D.melanogaster* hsp70—and of the human hsp70—*E. coli* β-galactosidase hybrid genes in plasmids 522 and 173, respectively, has been described previously (23,24).

Plasmid R81: plasmid A/PR 8/ms/34 (Mount Sinai) clone 4.76 which contains, in between a HindIII (5' end of the inserted gene) and a BamHI site, an influenza virus haemagglutinin gene, including short segments of 5' and 3' non-translated sequences was obtained from G. Brownlee. This DNA was digested with BamHI, and cohesive ends were filled in with DNA polymerase fragment A. The DNA was digested further with HindIII, and the haemagglutinin gene fragment was isolated. Vector pSVOd (28) was cut with SalI, and following incubation with DNA polymerase fragment A, was digested further with HindIII, and then ligated to the above haemagglutinin gene fragment to give plasmid R81.

A 650 bp Sau3A fragment was isolated from plasmid 51 (16). This fragment which included about 400 bp of promoter sequence of a *D.melanogaster* hsp70 gene, a complete RNA leader region and the first seven hsp70 codons was inserted into the unique BamHI site at the 5' end of the lac operon segment in plasmid MC1403 (6) to give plasmid RV15. Plasmid RV15 DNA was digested with SamI and SalI, and a 7 kb long fragment, including the above-mentioned 650 bp hsp70 gene segment and the lac operon segment, was isolated. Plasmid SVOd DNA was digested with BamHI, and the cohesive ends were filled in by DNA polymerase fragment A. The DNA was then digested with SalI and ligated to the purified 7 kb hybrid gene fragment to give plasmid 520.

Plasmid R84: p520 was digested with NcoI and PvuII, and a fragment of about 1 kb was isolated which included part of the pSVOd SV40 origin of replication segment, 400 bp of D.melanogaster hsp70 gene promoter and 65 bp of hsp70 gene RNA leader sequences. Plasmid R81 was digested with HindIII, ends filled as above, and the DNA was then further digested with NcoI, which cuts within the SV 40 origin of replication sequence, and then ligated to the isolated p520 fragment.

Plasmid 522-lys: p522 DNA was digested with BamHI and, partially, with PstI, and a 3.5 kb fragment containing pSVOd sequences including the SV40 origin of replication sequence, D.melanogaster hsp70 gene promoter sequences and 90 bp of hsp70 gene RNA leader region was isolated. A 0.9 kb PstI/BamHI fragment from plasmid pTKLys (21, obtained from A. Colman), which included a cDNA copy of the chicken lysozyme gene and short stretches of 5' and 3' nontranslated sequence, was ligated to the above p522 fragment to give p522-lys.

Plasmid 17-lys: DNA of plasmid 17 which contains a fragment of a human hsp70 gene (see map in ref.42) was digested with BglII and SacI and then treated with DNA polymerase fragment A. A 1.2 kb long fragment containing a functional heat shock promoter was isolated. This fragment was ligated to a 2.8 kb long pSP65 (29) HindIII/PvuII fragment that had been blunt-ended as above. The resulting construct p17–65 was then digested with EcoR1 and HindIII, and the larger of the two restriction fragments (4 kb) was isolated. Plasmid 522-lys was digested with EcoR1 and partially with HindIII, and a 1.5 kb fragment including the lysozyme gene and pSVOd vector sequences (containing the origin of replication region) was isolated and ligated to the above p17–65 fragment.

Plasmid p17hGH dhfr: p17 DNA was digested with EcoR1, blunt ended, and digested further with HindIII. A 3.25 kb fragment containing 3.15 kb of 5' nontranscribed sequence and about 110 bp of RNA leader sequence of a human hsp70 gene was isolated and ligated to a 2.8 kb PvuII/HindIII fragment from pSP65. DNA of the resulting construct was digested with BglII and partially with BamHI, and then religated to give p17Jo (the latter step eliminated all but a small region of the 5' nontranscribed sequence of the hsp70 gene). A human growth hormone cDNA gene (obtained from Celltech Ltd., Slough, G. B.) was subcloned into the unique BamHI site of pSP65 to give phGH. This plasmid was then digested with HindIII and SacI (both sites are from the polylinker), and the hGH fragment was isolated and inserted in between the same sites of p17Jo to give p17hGH. Plasmid p17hGH6 was derived by digesting p17hGH with NcoI and XbaI followed by treatment with DNA polymerase fragment A and religation (this step deletes 6 bp between the hGH and hsp gene sequences).

Finally, p17hGH6 was digested with EcoR1 and BamHI. A 1.2 kb fragment, containing hGH and hsp70 gene promoter and RNA leader sequences was isolated and inserted between the EcoR1 and the BamH1 site of pSV2-dhfr (40).

For the above experiments methods analogous to those described by Maniatis et.al. (26) were used. Plasmid DNAs were prepared by cesium chloride gradient centrifugation of cleared lysates.

Cell cultures, transfection, and Microinjection into Xenopus Oocytes

COS 1 African Green Monkey kidney, human Wish, and 293 cells, were grown in Dulbecco's modified Eagle's medium (Gibco), Chinese hamster ovary (CHO) cells in Ham's nutrient mixture F12 (KC Biologicals) and Drosophila melanogaster S3 cells in Schneider's Drosophila medium (KC Biologicals). All cells were grown in the presence of 10% calf serum. $CaCl_2$—or DEAE-dextran-based procedures (12, see also ref. 1) were used to transfect the different cell types used in this study (10–20 g DNA per 10 cm dish). Prior to expression analysis, transfected COS 1 cells were incubated for two days at 37° C. to permit amplification of the introduced plasmids. Other transfected cells were used in experiments after overnight incubation. Injections into sets of 10–20 Xenopus oocytes were carried out as described previously (41). Oocytes were injected with 2–5 ng of DNA in a volume of 10 nl.

Analysis of Hybrid Gene Products by Immunological Procedures a. ELISA assays

Cell extracts were prepared by repeated pipeting in buffer containing 0.5% NP40. Concentrations of hybrid gene products were measured by a classical ELISA procedure (43) employing rabbit and mouse anti-E. coli β-galactosidase antibodies, and peroxidase-conjugated rabbit anti-mouse Ig antibodies, the latter from DAKO Co.

b. Immunoprecipitation and Gel Analysis of Radioactively Labelled Hybrid Gene Products To metabolically label proteins, the normal medium was removed from COS 1 or CHO cell cultures and replaced by 2 ml/10 cm dish of methionine-free medium containing 200 Ci opf $^{35}$S-methionine. Following overnight incubation at 37° C., the cells were harvested and lysed. Immunoprecipitation and electrophoresis of the precipitated gene products were carried out according to standard procedures (14,22). Beat-treated or untreated Xenopus oocytes were labeled by overnight incubation at 21° C. in 200 l OR2 buffer per 10 oocytes (41) containing 100 Ci of $^{35}$S-methionine. Rabbit anti-haemagglutinin antiserum was provided by M. Thibon (Pasteur Institute, Paris), and rabbit anti-human pituitary growth hormone serum was obtained from DAKO Co.

c. Single Cell β-glactosidase Immunoassy

Cells were grown in 3.5 cm polystyrene culture dishes. The medium was removed, and the cells were washed twice with phosphate-buffered saline (PBS). Two ml of cold ethanol-acetic acid (99:1) were added, and the cells were left on ice for 30 min. The fixing solution was removed, and the cells were washed two more times with PBS. The dishes were then treated with 2 ml of 3% bovine serum albumin (BSA) in PBS for 15 min. at room temperature. After removal of the BSA solution, the dishes were incubated for 2 hrs. at room temperature with 1 ml of 60 g/ml rabbit anti-β-galactosidase antibodies (purified immunoglobulin fraction) in PBS with 0.1% BSA. The first antibody was removed by 3 washes with PBS, and 1 ml of 60 g/ml peroxidase-conjugated swine anti-rabbit Ig (DAKO Co.) in PBS—0.1% BSA was added. After 90 min. of incubation at room temperature, the cells were washed 4 times, and stained with 100 l of 0.01% orthodianisidin and 0.01% hydrogen peroxide in 10 mM phosphate buffer, pH 6.0. The reaction indicating the presence of β-galactosidase results in coloration of the positive cells within 15–30 min.

RESULTS

Hybrid Gene Constructions

FIG. 1 presents the DNA constructs with the selected genes under the expression control of heat shock promoter elements derived from *D.melanogaster* and human cells. In the case of *E. coli* β-galactosidase, restriction sites occuring early in the hsp70-coding sequences have been exploited to make hybrid genes that encode fusion proteins. Sufficient coding sequence is retained in the hybrid genes to ensure enzymatic activity of β-galactosidase. The *D.melanogaster* heat-shock gene fragment is fused at amino acid 7 of its coding sequence to the truncated β-galactosidase gene to give plasmid 522 (23), and the human gene fragment at amino acid 124 of its respective coding sequence, yielding plasmid 173 (42).

A human influenza virus haemagglutinin gene was placed under *D.melanogaster* heat-shock control in pR84. A chicken lysozyme gene has been incorporated into constructs using either *D.melanogaster* (p522-lys) or human (p17-lys) heat-shock gene promoters and a human growth hormone gene into a construct with a human heat-shock gene promoter (p17hGH dhfr). The vector sequences present in p522, pR84, p522-lys, p17-lys and p17hGH dhfr include a Simian Virus 40 (SV40) origin of replication fragment, permitting amplification of the plasmid constructs in COS monkey cells (11,28).

Expression Experiments with Xenopus Oocytes

DNA constructs to be tested for heat-shock expression control were microinjected into Xenopus oocyte nuclei. Ten min. after injection, oocytes were subjected to a heat shock of 90 min. at 36° C., followed by incubation at 21° C. for 12 hrs. in the presence, in the case of the immunoprecipitation experiments described below, of $^{35}$S-labelled methionine.

Measurements of gene expression under heat-shock control of the μgalactosidase constructs have been reported before (1,23,30,42). In those experiments, levels of β-galactosidase had been quantified by means of a standard colorimetric activity assay. Heat treatment of hybrid gene-containing oocytes resulted in about a 30-fold increase in the level of β-galactosidase produced.

In the case of constructs containing a *D.melanogaster* hsp70 gene promoter we have been able to demonstrate (30) that the accumulation of β-galactosidase in heat-shocked oocytes is dependent on a functional heat shock gene promoter and cannot be explained merely as a consequence of preferential translation during (27,31,39), or following, heat shock of hybrid gene products that may have arisen from read-through transcription. The upstream promoter element required for heat-regulated transcription in Xenopus as well as in COS monkey cells lies 48 to 62 bp upstream from the start of transcription site of the hsp70 gene (32,34). Our own studies with hsp70-β-galactosidase hybrid genes with promoter segments of different lengths have indicated that 67 bp but not 50 bp of promoter sequence are sufficient for high level heat-regulated synthesis of μgalactosidase in Xenopus oocytes (30; Ananthan and Voellmy, unpublished results). Thus, the efficient, heat-induced synthesis of the protein products of hsp hybrid genes such as the one in p522 is under the control of the heat-shock transcription signal. A gene lacking this signal is essentially inactive at heat shock and control temperature. Identical results were obtained from analogous experiments with COS monkey cells (1).

The β-galactosidase hybrid genes encode hsp70-β-galactosidase fusion proteins. Thus, in these constructs the RNA leader regions, and the sequences around and including the translation initiation sites, are from heat-shock genes. Such fusion proteins, however, will not be acceptable gene products for most practical applications; the synthesis of the authentic product of a gene of interest will be required. For this reason all constructs with eucaryotic protein genes had been prepared by joining heat-shock gene fragments, and protein-coding genes to be expressed, within their RNA leader regions.

Expression experiments with such constructs are shown in FIG. 2. The presence of labelled protein products was demonstrated by immunoprecipitation of Xenopus oocyte extracts or suspension media, using either anti-haemagglutinin, anti-chicken lysozyme or anti-human growth hormone sera. Immunoprecipitated proteins were analyzed by electrophoresis on SDS-polyacrylamide gels. Extracts from hybrid gene-containing oocytes are analyzed in FIG. 2a: lysozyme antibodies precipitate a 14.3 kd polypeptide which coelectrophoreses with a chicken lysozyme standard. Both p17-lys and p522-lys only give rise to significant synthesis of lysozyme protein after a heat shock (lanes 4 and 6); plasmid-injected oocytes that have not sustained a heat shock produce little or no lysozyme (lanes 3 and 5). Injection of pR84 and immunoprecipitation with anti-haemagglutinin antibody reveals the presence of a polypeptide of about 75 kd, the expected molecular weight of the unprocessed influenza virus haemagglutinin (lanes 1 and 2). Again, detectable amounts of gene product are only made in heat-treated oocytes.

Anti-human growth hormone serum specifically precipitates a protein of 21 kd in heat-treated but not in untreated oocytes containing p17hGH dhfr DNA (lanes 14 and 15). The molecular weight of the recombinant gene product is identical to that of human growth hormone.

FIG. 2b indicates the results obtained with suspension media from the same experiments; it can be seen that lysozyme produced under heteroplogous heat-shock control, either Drosophila or human, is secreted by the oocytes into the suspension medium (lanes 1 to 4). The same holds for human growth hormone (lanes 5 and 6). It may be worth noting that human growth hormone represents a substantial fraction of all newly synthesized proteins secreted into the medium. Aliquots of suspension medium have been analyzed, without immunoprecipitation, in lanes 7 (heat shock) and 8 (control).

We conclude from these results that heat-shock promoter activity does not require the presence of a complete heat shock RNA leader region. The haemagglutinin construct contains only about 65 bp of the 250 bp long *D.melanogaster* hsp70 RNA leader. The presence of foreign non-protein-coding or protein-coding sequences downstream from the hsp RNA leader segment does not appear to affect adversely either promoter function or hybrid product translation: all the different constructs yield significant amounts of protein products. Since neither the *D.melanogaster* nor the human hsp70 RNA leader segment contains an ATG codon, the translation initiation signals must have been provided by the different protein-coding genes. The above electrophoretic analysis of the hybrid gene products strongly suggests that the normal start codons of the various foreign protein-coding genes are being recognized properly even when present in hsp hybrid gene RNAs. It may be worth noting that since the protein-coding genes are the source of the translation initiation signals used, their specific properties obviously define, at least in part, the expression characteristics of the hsp hybrid genes. To obtain optimal expression results, it may, therefore, be necessary in some cases to replace inefficient translation start signals by more suitable ones (see for example the construction of p17hGH dhfr in Materials and Methods).

That both chicken lysozyme and human growth hormone, that have been synthesized under heat-shock control, are secreted from the producer cells, is an important demonstration of the practicality of the use of heat-shock expression systems. Apparently, heat treatment does not inactivate any of the steps involved in protein secretion. Also, heat-shock control elements linked to genes encoding secretable proteins do not in any way interfere with the export of the products of these genes (none of the heat-shock proteins is itself a secretable protein).

We assume that the observation that haemagglutinin is produced but not processed in Xenopus oocytes indicates the absence of the appropriate modifying activities in these cells. Analogous results had been obtained for the synthesis of the protein under the control of an SV40 promoter (or a metallothionein gene promoter, 36) in COS monkey cells or in bovine Papilloma virus-transformed mouse cells (10,36).

Expression of Hybrid Genes Under Heat-Shock Control in COS Monkey Cells

Immunological evidence for the synthesis of E. coli -specific β-galactosidase in p522-transfected COS cells is presented in FIG. 3. Transfected, heat-treated or untreated cells were incubated overnight at 37° C. in the presence of $^{35}$S-methionine. Protein extracts were used for immunoprecipitation with either μgalactosidase antibodies or bromelain-specific antiserum as a control. Whereas no polypeptide of the expected molecular weight (about 130 kd) was precipitated with control antiserum (lanes 1 and 2), β-galactosidase-specific antibodies precipitated such a polypeptide, and this only with extracts from heat-shocked cells (lanes 3 and 4). Lanes 5 to 16 show a similar experiment with cells transfected with p522-lys, p17-lys and p17hGH dhfr. The cells were labeled as indicated in Materials and Methods, and both cell extracts (not shown) and growth media (lanes 5–16) were analyzed as above with lysozyme- and growth hormone-specific antisera. A labeled protein with a molecular weight identical to that of a lysozyme standard (14.3 kd) is clearly visible in media samples from cells transfected with p522-lys or p17-lys that have undergone a heat shock (lanes 5 to 8). This protein was absent from samples derived from p522-transfected cells (lanes 9 and 10).

Analogous results were obtained with p17hGH dhfr-containing COS cells. A labeled protein of molecular weight identical to that of authentic growth hormone could be immunoprecipitated from media samples of heat-shocked cells (lane 12). A sample from p17-lys-transfected cells served as control in this experiment (lane 11).

Similar findings were made with Chinese Hamster ovary cells (CHO) that had been transfected with a human growth hormone hybrid gene (lanes 15 and 16).

Transfection of Cells in Culture: Single Cell Assay for the Transient Expression of hsp-β-galactosidase hybrid genes Our previous studies using heat-shock control of β-galactosidase synthesis (23) have suffered from a lack of knowledge concerning the fraction of cells actually participating in the expression of hybrid genes. It occurred to us that one could directly ascertain which cells are actually synthesizing β-galactosidase under heat-shock control by using an immunological staining procedure after fixation of cultured cells (see Materials and Methods). FIG. 4 shows the application of this procedure to a variety of eucaryotic cell types transfected by p522 or p173; it can clearly be seen that cells successfully transfected with these expression plasmids can be differentiated from nontransfected cells. The red to brown coloration of cells observed under the microscope is an indication of the β-galactosidase activity in these cells.

Our data suggest that this single cell assay of hsp-β-galactosidase gene expression provides a general and convenient procedure for directly demonstrating transfection efficiencies of apparently any eucaryotic cell type. This notion is further supported by observations of other groups that a D.melanogaster hsp70 gene promoter is even active in yeast and probably even in plant cells (24).

The combination of the above procedure and total μgalactosidase measurements either by the colorimetric activity assay or by an appropriate ELISA technique could therefore be used to quantitate the performance of heat-shock expression vectors in transient expression studies. As an example, for such a quantitation we have estimated the amounts of E. coli-specific β-galactosidase produced in heat-shocked D.melanogaster S3 cells transfected with plasmid 522. By an ELISA procedure we found that approximately 150 ng of β-galactosidase are made in a transfected culture containing about $10^7$ cells during a 3 hr exposure at 37° C. The transfection efficiency was estimated to be about 0.01%. Thus, each transfected cell makes about 0.15 ng of E. coli-specific β-galactosidase.

REMARKS

In this Example 3 we have described the use of promoter elements derived from both Drosphila and human hsp70 genes for the expression of a number of genes in both homologous and heterologous cell types. We have chosen to employ both genes encoding non-secretable proteins, E. coli β-galactosidase and a human influenza haemagglutinin, as well as genes encoding secretable proteins such as chicken lysozyme and human growth hormone. We have observed that both Drosophila and human heat-shock gene constructions can direct the synthesis of, for instance, lysozyme protein in the heterologous Xenopus oocyte system; in addition, both expression units are strictly heat shock-dependent in this system and give rise to comparable levels of lysozyme synthesis. This heterologous system has, in addition, been shown to permit the secretion out of the oocyte of lysozyme and human growth hormone produced after a period of heat shock. Similar studies indicate that a wide range of cell types can be used in an analogous fashion.

Our approach to the estimation of the level of heat shock-controlled gene expression also makes use of the broad range of cell types in which the simple β-galactosidase test can be performed at the single cell level. This procedure has obvious advantages in its direct approach over other techniques such as dominant selection using, for instance, neomycin resistance genes (38). Other direct cell assays for transfection, such as co-transfection with plasmids expressing SV40 T-antigen, followed by an immunofluorescence test for T-antigen, are limited to cell types capable of expressing T-antigen efficiently.

All expression data presented in this application have been obtained from transient studies. A number of lines of evidence, in addition to our ongoing studies, indicate that heat-shock expression control of heterologous genes can also be expected to operate in an inducible fashion with constructs that are integrated into the cell genome. Earlier data have demonstrated that entire Drosophila hsp70 genes could be stably integrated, and expressed under heat-shock control in recipient mouse cells (7). More recently hybrid hsp70-lac Z and hsp70-alcohol dehydrogenase genes have been stably introduced into the Drosophila germline (3,20, 25) by P-element-mediated transfection. In these experiments it has been demonstrated elegantly that hybrid gene activity in the Drosophila transformants remains inducible by heat shock in a widespread distribution amongst the tissues of both larvae and adult flies.

The stability of the heat-induced expression of β-galactosidase has been established in this application to hold even for the highly amplified situation in COS cells and in Xenopus oocytes; in addition we have obtained results confirming the high degree of inducibility of heat shock-dependent synthesis of a secretable human protein using the amplified, generally episomal, bovine Papilloma virus system in mouse C-127 cells (unpublished results). We are presently performing experiments to further establish this high degree of inducible expression in dihydrofolate reductase (dhfr)-deficient Chinese hamster ovary (CHO) cells using the co-amplification procedure, under methotrexate selection, of constructs carrying the dihydrofolate reductase gene. The single cell staining experiments shown in FIG. 4 indicate the establishment of the inducible capacity of β-galactosidase expression in Drosophila cell cultures at four and seven days (one month also, data not shown) after transfection. The evidence that, even though no selective pressure has been applied, progeny cells surrounding initially transfected cells also inducibly synthesize β-galactosidase further indicates the potential long-term applicability of this expression system. The general aim of our development is to establish a eucaryotic expression system that can be optimally applied to the large-scale synthesis of eucaryotic proteins of interest. It is now generally accepted that many complex proteins which normally undergo specific posttranslational modifications, such as glycosylation, cannot be correctly synthesized by genetically engineered procaryotes. Of the conceivable eucaryotic expression systems, a number of criteria define their general usefulness and applicability. An optimal system should be of general application in a variety of human and related cell types, particularly where cell type-specific modifications are important for the biological competence of such proteins.

The system should be acceptable from the points of view of efficiency of gene expression, as well as concerning safety considerations of host cells or vector systems. Finally, since there are frequently problems with cell growth and expansion when such cells are producing large quantities of vital antigens or enzymes, both of which may prove toxic to the cells, a fully inducible expression system is of great advantage. Such an inducible system must, for large-scale application, permit the induction of gene expression by practicable procedures, and these irrespective of the cell culture system employed. Various of the available expression systems using SV40, adenovirus, Rous Sarcoma Virus (RSV), mouse mammary tumor virus (MMTV) and metallothionein promoters appear to fulfill some of the above-mentioned criteria for a generally applicable and acceptable expression system. None, however, fulfill all of these important criteria; SV40, adenovirus, and RSV promoters are constitutive, metallothionin promoters appear to be barely inducible (33), and the MMTV promoter although inducible is so in a less than totally practicable fashion. MMTV, RSV, SV40 and adenovirus elements are derived from tumor viruses, and in addition not all of these promoters, or their habitual vector systems, are functional in a wide variety of cell types.

The characterics of broad host cell range, safety, efficiency, and high degree of inducibility under simple conditions of heat shock make the described eucaryotic expression system of particular interest for biotechnological applications in the field of human medicine.

Although the foregoing invention has been described in some detail, by way of illustration and example for purposes of clarity and understanding, it will be obvious that certain changes and modifications may be practiced within the scope of the appended claims.

Literature Cited to Illustrate the State of the Art

The following references, though not essential to an understanding of the invention disclosed herein, are disclosed for purposes of indicating the background of the invention and for purposes of illustrating the state of the art.

1. Amin, J., Mestril, R., Lawson, R., Klapper, H. and R. Voellmy. 1985. The Heat Shock Consensus Sequence is not Sufficient for hsp70 Gene Expression in *D.melanogaster*. Mol. Cell. Biol. 5: 197–203.
2. Arrigo, A.-P. 1981. Ph.D. Thesis, University of Geneva, Switzerland.
3. Bonner, J. J., Parks, C., Parker-Thornburg, J., Mortin, M. A. and H. R. B. Pelham. 1984. The Use of Promoter Fusions in Drosophila genetics: Isolation of Mutations Affecting the Heat Shock Response. Cell 37: 979–991.
4. Brazzell, C. and T. D. Ingolia. 1984. Stimuli that Induce a Yeast Heat Shock Gene Fused to β-galactosidase. Mol. Cell. Biol. 4: 2573–2579.
5. Buetti, E. and H. Diggelmann. 1981. Cloned Mouse Mammary Tumor Virus DNA is Biologically Active in Transfected Mouse Cells and its Expression is Stimulated by Glucocorticoid Hormones. Cell 23: 335–345.
6. Casadaban, M. J., Chou, J. and S. N. Cohen. 1980. In Vitro Gene Fusions that Join an Enzymatically Active β-galactosidase Segment to Aminoterminal Fragments of Exogenous Proteins: *Escherichia Coli* Plasmid Vectors for the Detection and Cloning of Translational Initiation Signals. J. Bacteriol. 143: 971–980.
7. Corces, V., Pellicer, A., Axel, R. and M. Meselson. 1981. Integration, transcription, and control of a Drosophila Beat Shock Gene in Mouse Cells. Proc. Natl. Acad. Sci. USA 78: 7038–7042.
8. DiNocera, P. P. and L Dawid. 1983. Transient Expression of Genes Introduced into Cultured Cells of Drosophia. Proc. Natl. Acad. Sci. USA 80: 7095–7098.
9. Finkelstein, D. B. and S. Strausberg. 1983. Heat Shock-regulated Production of *Escherichia Coli* β-galactosidase in *Saccharomyces Cerevisiae*. Mol. Cell. Biol. 3: 1625–1633.
10. Gething, M. J. and J. Sambrook. 1981. Cell Surface Expression of Influenza Hemagglutinin from a Cloned DNA copy of the RNA Gene. Nature 293: 620–625.
11. Gluzman, Y. 1981. SV40-transformed Simian Cells Support the Replication of Early SV40 Mutants. Cell. 23: 175–182.
12. Graham, F. L. and A. J. van der Eb. 1973. A New Technique for the Assay of Infectivity of Human Adenovirus 5 DNA. Virol. 52: 456–467.
13. Gralnik, H. R., Williams, S. B., and M. E. Rick. 1983. Role of Carbohydrate in Multimeric Structure of Factor VIII/von Willebrand Factor Protein. Proc. Natl. Acad. Sci. USA 80: 2771–2774.
14. Guillouzo, A., Feldmann, G. and M. Bolsnard. 1976. Preparation of Liver Explant Cultures for the Demonstration of Intracellular Proteins. In: First International Symposium of Immunoenzymatic Techniques, INSERM Symposium 2 (Feldmann et.al., eds.), N. Holland Publishing Co., Amsterdam.

15. Hynes, N., van Ooyen, A. J. J., Kennedy, N., Herrlich, P., Ponta, H. and B. Groner. 1983. Subfragments of the Large Terminal Repeat Cause glucocorticoid-responsive Expression of Mouse Mammary Tumor Virus and of an Adjacent Gene. Proc. Natl. Acad. Sci. USA 80: 3637–3641.

16. Karch, F., Torok, I. and A. Tissieres. 1981. Extensive Regions of Homology in Front of the Two hsp70 Heat Shock Variant Genes in *Drosophila Melanogaster*. J. Mol. Biol. 148: 219–230.

17. Karin, M. and R. Richards. 1982. Human Metallothionein Genes—Primary Structure of the Metallothionein-II Gene and a Related Process Gene. Nature 308: 513–519.

18. Karin, M., Haslinger, A., Holtgreve, H., Richards, R. I., Krauter, P., Westphal, H. M. and M. Beato. 1984. Characterization of DNA Sequences through which Cadmium Glucocorticoid Hormones Induce Human Metallothionein IIA Gene. Nature 308: 513–519.

19. Kaufman, R. J., Wasley, L. C., Spiliotes, A. J., Gossels, S. D., Latt, S. A., Larson, G. R. and R. M. Kay. 1985. Coamplification and Coexpression of Human Tissue-Type Plasminogen Activator and Murine Dihydrofolate Reductase Sequences in Chinese Hamster Ovary Cells. Mol. Cell. Biol. 5: 1750–1759.

20. Klemenz, R., Hiltmark, D. and W. J. Gehring. 1985. Selective Translation of Heat-Shock mRNA in *Drosophila Melanogaster* Depends on Sequence Information in the Leader. EMBO J. 4: 2053–2060.

21. Krieg, P., Strachan, R., Wallis, E., Tabe, L. and A. Colman. 1984. Efficient Expression of Cloned Complementary DNAs for Secretory Proteins after Injection into Xenopus Oocytes. J. Mol. Biol. 180: 615–643.

22. Laemmli, U.K. 1970. Cleavage of Structural Proteins During the Assembly of the Head of Bacteriophage T4. Nature 227: 680–685.

23. Lawson, R., Mestril, R., Schiller, P. and R. Voellmy. 1984. Expression of Heat-Shock-β-galactosidase Hybrid Genes in Cultured Drosophila cells. Mol. Gen. Genet. 198: 116–124.

24. Lis, J., Costlow, N., deBanzie, J., Knipple, D., O'Connor, D. and L. Sinclair. 1982. Transcription and Chromatin Structure of Drosophila Heat-Shock Genes in Yeast. In: Heat-Shock from Bacteria to Man (Schlesinger et.al., eds.), Cold Spring Harbor Laboratory, N.Y., 57–62.

25. Lis, J. T., Simon, J. A. and C. A. Sutton. 1983. New Heat-Shock Puffs and β-galactosidase Activity Resulting from Transformation of Drosophila with an hsp70-lacZ Hybrid Gene. Cell 35: 403–410.

26. Maniatis, T., Fritsch, E. and J. Sambrook. 1982. Molecular Cloning. Cold Spring Harbor Laboratory, N.Y.

27. McKenzie, S. L., Henikoff, S. and M. Meselson. 1975. Localization of RNA from Heat-induced Polysomes at Puff Sites in *Drosophila Melanogaster*. Proc. Natl. Acad. Sci. USA 72: 1117–1121.

28. Mellon, P., Parker, V., Gluzman, Y. and T. Maniatis. 1981. Identification of DNA Sequences Required for Transcription of the Human 1-globin Gene in a New SV40 Host-vector System. Cell 27: 279–288.

29. Melton, D. A., Krieg, P. A., Rebagliati, M. R., Maniatis, D., Zinn, K. and M. R. Green. 1984. Efficient In Vitro Synthesis of Biologically active RNA and RNA Hybridization Probes From Plasmids Containing a Bacteriophage SP6 Promoter. Nucleic Acids Res. 12: 7035–7056.

30. Mestril, R., Rungger, D., Schiller, P. and R. Voellmy. 1985. Identification of a Sequence Element in the Promoter of the Drosophila hsp23 Gene that is Required for its Heat Activation. EMBO J, in press.

31. Mirault, M.-E., Goldschmidt-Clermont, M., Moran, L., Arrigo, A.-P. and A. Tissieres. 1978. The Effect of Heat-Shock on Gene Expression in *Drosophila Melanogaster*. Cold Spring Harbor Symp. Quant. Biol. 42: 819–827.

32. Mirault, M.-E., Southgate, R. and E. Delwart. 1982. Regulation of Heat-Shock Genes: A DNA Sequence Upstream of Drosophila hsp70 Genes is Essential for Their Induction in Monkey Cells. EMBO J. 1: 1279–1285.

33. Pavlakis, G. N. and D. H. Hamer. 1983. Regulation of a Metallothionin-Growth Hormone Hybrid Gene in Bovine Papilloma Virus. Proc. Natl. Acad. Sci. USA 80: 397–401.

34. Pelham, H. R. B. 1982. A Regulatory Upstream Promoter Element in the Drosophila hsp70 Heat-Shock Gene. Cell 30: 517–528.

35. Pelham, H. R. B. and M. Bienz 1982. Expression of a Drosophila Heat-Shock Protein in Xenopus Oocytes: Conserved and Divergent Regulatory Signals. EMBO J. 1: 1583–1588.

36. Sambrook, J., Rodgers, L., White, J. and M.-J. Gething. 1985. Lines of BPV-transformed Murine Cells that Constitutively Express Influenza Virus Hemagglutinin. EMBO J. 4: 91–103.

37. Schlesinger, M. J., Ashburner, M. and A. Tissieres, eds. 1982. Heat-Shock from Bacteria to Man. Cold Spring Harbor Laboratory, New York.

38. Southern, P. and P. Berg. 1982. Mammalian Cell Transformation with SV40 Hybrid Plasmid Vectors. In: Eucaryotic Vital Vectors (Y. Gluzmann ed.), Cold Spring Harbor Laboratory, New York. 41–45.

39. Spradling, A., Pardue, M.-L. and S. Penman. 1977. Messenger RNA in Heat-Shocked Drosophila Cells. J. Mol. Biol. 109: 559–587.

40. Subramani, S., Mulligan, R., and P. Berg. 1981. Expression of the Mouse Dihydrofolate Reductase Complementary Deoxyribonucleic Acid in Simian Virus 40 Vectors. Mol. Cell. Biol. 1: 854–864.

41. Voellmy, R. and D. Rungger. 1982. Transcription of a Drosophila Heat-Shock Gene is Heat-Induced in Xenopus Oocytes. Proc. Natl. Acad. Sci. USA 79: 1776–1780.

42. Voellmy, R., Ahmed, A., Schiller, P., Bromley, P. and D. Rungger. 1985. Isolation and Functional Analysis of a Human 70000 Dalton Heat-Shock Protein Gene Segment. Proc. Natl. Acad. Sci. USA 82: 4949–4953.

43. Voller, A., Bartlett, A. and D. E. Bidwell. 1978. Enzyme Immunoassays with Special Reference to ELISA Techniques. J. Clin. Pathol. 31: 507–520.

Deposits

The following deposits were made by applicant at the ATCC in Rockville, Md.:

| | |
|---|---|
| *E. coli*, PR84 | Accession #39595 |
| *E. coli*, RV15 | Accession #39597 |
| *E. coli*, 629 | Accession #39598 |

The following deposits were made by applicant at the National Collection of Industrial and Marine Bacteria Ltd., P.O. Box No. 31, 135 Abbey Road, Aberdeen, AB° SDG, Scotland:

|   |   | NCIB # |
|---|---|---|
| E. coli | HB101 p522-lys | 12175 |
| E. coli | 1106 p17-lys | 12176 |
| E. coli | HB101 p17-hGH.neo | 12122 |
| E. coli | HB101 p17-hGH | 12123 |
| E. coli | HB101 p17-hGH.Δ.6dhfr | 12124 |
| E. coli | HB101 p17-hGH.Δ.6 | 12125 |

Upon issuance of this application, all restrictions on availability of the above culture deposits at the ATCC and NCIB will be removed, making the same available to the public.

We claim:

1. A method for producing competent gene translation products, said method comprising the steps of:
   a) providing a DNA construct in which a foreign structural gene encoding for a protein of interest is operably linked to the promoter of an eukaryotic heat-shock gene,
   b) introducing said DNA construct in host cells either by transformation or by transfection to form transformed or transfected host cells,
   c) subjecting said transformed or transfected host cells to a transient shift up in temperature and permitting translation to occur after the temperature has been returned to the normal growth temperature of said host cells, whereby the production of said protein of interest occurs,
   d) recovering said protein of interest.

2. The method of claim 1, wherein said foreign structural gene and said promoter are operably linked in an expression vector having at least an extrachromosomal replication system which allows multiplication of said DNA construct in said host cells.

3. The method of claim 1, wherein said DNA construct further comprises at least one selectable marker gene which allows for selection of transformed or transfected host cells and which can further be an amplifiable gene.

4. A method for producing competent gene translation products, said method comprising the steps of:
   a) providing a DNA construct in which a foreign structural gene encoding for a protein of interest is operably linked to the promoter of a heat-shock gene which encodes a 70 kilo-dalton heat-shock protein of Drosophila melanogaster,
   b) introducing said DNA construct in host cells either by transformation or by transfection to form transformed or transfected host cells,
   c) subjecting said transformed or transfected host cells to a transient shift up in temperature and permitting translation to occur after the temperature has been returned to the normal growth temperature of said host cells, whereby the production of said protein of interest occurs,
   d) recovering said protein of interest.

5. The method of claim 4, wherein said heat-shock gene comes from a different eukaryotic species from said host cell.

6. The method of claim 1, wherein said foreign structural gene is a mammalian gene.

7. The method of claim 6 wherein said host cells are mammalian cells.

8. The method of claim 6 wherein said foreign structural gene is a human gene.

9. The method of claim 8, wherein said host cells are mammalian cells.

10. The method of claim 9, wherein said mammalian cells are COS-I cells.

11. The method of claim 1, wherein said DNA construct is formed by fusion of said promoter with said foreign structural gene by means of the untranslated 5' sequences located between the promoter sequences and the translated sequences of said genes.

12. The method of claim 1, wherein said DNA construct is formed by fusion of said promoter with a fragment of the heat-shock gene which follows said promoter and with at least a fragment of said foreign structural gene.

13. The method of claim 1, wherein said DNA construct further comprises a terminal 3' untranslated sequence of the heat-shock gene or of another gene.

14. A method for producing competent gene translation products, said method comprising the steps of:
   a) providing a DNA construct in which a foreign structural gene encoding for a protein of interest is operably linked to the promoter of a heat-shock gene which encodes a 70 kilo-dalton heat-shock protein in humans,
   b) introducing said DNA construct in host cells either by transformation or by transfection to form transformed or transfected host cells,
   c) subjecting said transformed or transfected host cells to a transient shift up in temperature and permitting translation to occur after the temperature has been returned to the permissive temperature, whereby the production of said protein of interest occurs,
   d) recovering said protein of interest.

* * * * *

UNITED STATES PATENT AND TRADEMARK OFFICE
CERTIFICATE OF CORRECTION

PATENT NO. : 5,646,010
DATED : July 8, 1997
INVENTOR(S) : Peter Bromley, et. al.

It is certified that error appears in the above-identified patent and that said Letters Patent is hereby corrected as shown below:

Title page, item [73], Assignee: change "Rockwell" to --Rothwell--.

Signed and Sealed this

Thirtieth Day of June, 1998

*Attest:*

BRUCE LEHMAN

*Attesting Officer*  *Commissioner of Patents and Trademarks*